United States Patent
Emanuel et al.

(10) Patent No.: US 8,992,979 B2
(45) Date of Patent: Mar. 31, 2015

(54) SUSTAINED-RELEASE DRUG CARRIER COMPOSITION

(75) Inventors: Noam Emanuel, Jerusalem (IL); Moshe Neuman, Ramat Gan (IL); Shlomo Barak, Tel Aviv (IL)

(73) Assignee: Polypid Ltd., Petach-Tikva (IL)

( * ) Notice: Subject to any disclaimer, the term of this patent is extended or adjusted under 35 U.S.C. 154(b) by 0 days.

(21) Appl. No.: 13/383,893

(22) PCT Filed: Jul. 14, 2010

(86) PCT No.: PCT/IL2010/000563
§ 371 (c)(1),
(2), (4) Date: Jan. 13, 2012

(87) PCT Pub. No.: WO2011/007353
PCT Pub. Date: Jan. 20, 2011

(65) Prior Publication Data
US 2012/0114756 A1    May 10, 2012

Related U.S. Application Data

(60) Provisional application No. 61/225,289, filed on Jul. 14, 2009.

(51) Int. Cl.
*A61K 9/00* (2006.01)
*A61P 19/08* (2006.01)
*A61P 35/00* (2006.01)
(Continued)

(52) U.S. Cl.
CPC ............ *A61K 9/1641* (2013.01); *A61K 9/1617* (2013.01); *A61K 9/1647* (2013.01); *A61L 24/0015* (2013.01); *A61L 27/34* (2013.01); *A61L 27/54* (2013.01); *A61L 31/10* (2013.01); *A61L 31/16* (2013.01); *A61L 2300/22* (2013.01);
(Continued)

(58) Field of Classification Search
None
See application file for complete search history.

(56) References Cited

U.S. PATENT DOCUMENTS 3,773,919 A    11/1973  Boswell et al.
4,522,803 A     6/1985  Lenk et al.
(Continued)

FOREIGN PATENT DOCUMENTS

EP    1098610 B1    4/2009
EP    2123274 A1   11/2009
(Continued)

OTHER PUBLICATIONS

Capito, Ramille M. et al., (2008) Self-assembly of large and small molecules into hierarchically ordered sacs and membranes. Science 319(5871):1812-1816.
(Continued)

Primary Examiner — Brian-Yong Kwon
Assistant Examiner — Jianfeng Song
(74) Attorney, Agent, or Firm — Fourth Dimension IP; Daniel Feigelson

(57) ABSTRACT

The present invention provides compositions for extended release of one or more active ingredients, comprising a lipid-saturated matrix formed from a non-biodegradable polymer or a block-co-polymers comprising a non-biodegradable polymer and a biodegradable polymer. The present invention also provides methods of producing the matrix compositions and methods for using the matrix compositions to provide controlled release of an active ingredient in the body of a subject in need thereof.

28 Claims, 6 Drawing Sheets

(51) Int. Cl.

| | |
|---|---|
| *A61P 29/00* | (2006.01) |
| *A61P 31/04* | (2006.01) |
| *A61K 31/56* | (2006.01) |
| *A61P 31/10* | (2006.01) |
| *A61K 9/16* | (2006.01) |
| *A61L 24/00* | (2006.01) |
| *A61L 27/34* | (2006.01) |
| *A61L 27/54* | (2006.01) |
| *A61L 31/10* | (2006.01) |
| *A61L 31/16* | (2006.01) |

(52) U.S. Cl.
CPC ...... *A61L2300/406* (2013.01); *A61L 2300/416* (2013.01); *A61L 2300/602* (2013.01)
USPC .......................... 424/486; 424/484; 514/169

(56) References Cited

U.S. PATENT DOCUMENTS

| | | | |
|---|---|---|---|
| 4,578,384 A | 3/1986 | Hollinger | |
| 4,882,167 A | 11/1989 | Jang | |
| 5,043,166 A | 8/1991 | Barenholz et al. | |
| 5,316,771 A | 5/1994 | Barenholz et al. | |
| 5,837,221 A | 11/1998 | Bernstein et al. | |
| 5,919,480 A | 7/1999 | Kedar et al. | |
| 6,048,551 A | 4/2000 | Hilfinger et al. | |
| 6,071,494 A | 6/2000 | Unger et al. | |
| 6,083,482 A | 7/2000 | Wang | |
| 6,120,805 A | 9/2000 | Spenlehauer et al. | |
| 6,156,337 A | 12/2000 | Barenholz et al. | |
| 6,162,462 A | 12/2000 | Bolotin et al. | |
| 6,238,702 B1 | 5/2001 | Berde et al. | |
| 6,248,345 B1 | 6/2001 | Goldenheim et al. | |
| 6,277,413 B1 | 8/2001 | Sankaram | |
| 6,287,587 B2 | 9/2001 | Shigeyuki et al. | |
| 6,333,021 B1 | 12/2001 | Schneider et al. | |
| 6,403,057 B1 | 6/2002 | Schneider et al. | |
| 6,787,132 B1 | 9/2004 | Gabizon et al. | |
| 6,793,938 B2 | 9/2004 | Sankaram | |
| 6,967,028 B2 | 11/2005 | Dulieu et al. | |
| 7,045,146 B2 | 5/2006 | Caruso et al. | |
| 7,160,554 B2 | 1/2007 | Zalipsky et al. | |
| 2001/0000470 A1 | 4/2001 | Bernstein et al. | |
| 2003/0113379 A1 | 6/2003 | Chen et al. | |
| 2003/0161809 A1* | 8/2003 | Houston et al. | 424/85.2 |
| 2003/0228355 A1 | 12/2003 | Zarif et al. | |
| 2004/0018327 A1 | 1/2004 | Wynn et al. | |
| 2004/0115240 A1 | 6/2004 | Narhi et al. | |
| 2004/0247624 A1* | 12/2004 | Unger et al. | 424/400 |
| 2005/0191344 A1 | 9/2005 | Zalipsky et al. | |
| 2005/0208100 A1 | 9/2005 | Weber et al. | |
| 2005/0249697 A1 | 11/2005 | Uhrich et al. | |
| 2005/0287180 A1 | 12/2005 | Chen et al. | |
| 2006/0073203 A1 | 4/2006 | Ljusberg-Wahren et al. | |
| 2006/0100370 A1* | 5/2006 | Wellisz et al. | 525/88 |
| 2006/0147520 A1 | 7/2006 | Ruegg | |
| 2006/0188573 A1 | 8/2006 | Imberg | |
| 2006/0189911 A1 | 8/2006 | Fukuhira et al. | |
| 2007/0112438 A1 | 5/2007 | Fukuhira et al. | |
| 2007/0141134 A1 | 6/2007 | Kosak | |
| 2007/0280991 A1* | 12/2007 | Glauser et al. | 424/426 |
| 2008/0085263 A1 | 4/2008 | Thuresson et al. | |
| 2008/0095849 A1 | 4/2008 | Wu et al. | |
| 2008/0119494 A1* | 5/2008 | Young et al. | 514/259.41 |
| 2009/0171077 A1 | 7/2009 | Hong et al. | |
| 2009/0259302 A1 | 10/2009 | Trollsas et al. | |
| 2009/0318355 A1 | 12/2009 | Chen et al. | |
| 2010/0196482 A1 | 8/2010 | Radovic-Moreno | |
| 2010/0266491 A1 | 10/2010 | Farokhzad et al. | |
| 2011/0117184 A1 | 5/2011 | Bromley et al. | |

FOREIGN PATENT DOCUMENTS

| | | |
|---|---|---|
| IL | 140899 | 5/2007 |
| JP | 61063613 A | 4/1986 |
| JP | 4018035 A | 1/1992 |
| JP | 4046115 A | 2/1992 |
| WO | 91/07171 A1 | 5/1991 |
| WO | 95/24929 A2 | 9/1995 |
| WO | 96/21470 A2 | 7/1996 |
| WO | 98/07412 A1 | 2/1998 |
| WO | 99/55306 A1 | 11/1999 |
| WO | 00/03660 A1 | 1/2000 |
| WO | 00/78357 A2 | 12/2000 |
| WO | 2008/124634 A1 | 10/2008 |
| WO | 2009006311 A2 | 1/2009 |
| WO | 2009/058666 A1 | 5/2009 |
| WO | 2009061515 A1 | 5/2009 |
| WO | 2009/110939 A2 | 9/2009 |
| WO | 2009/127060 A1 | 10/2009 |
| WO | 2010/007623 A1 | 1/2010 |
| WO | 2010/078517 A2 | 7/2010 |
| WO | 2010/135207 A1 | 11/2010 |
| WO | 2011/089595 A2 | 7/2011 |

OTHER PUBLICATIONS

Evora, Carmen et al., (1998) Relating the phagocytosis of microparticles by alveolar macrophages to surface chemistry: The effect of 1,2-dipalmitoylphosphatrdylcholine. Journal of Controlled Release 51(2-3): 143-152.
Heyes, James et al., (2005) Cationic lipid saturation influences intracellular delivery of encapsulated nucleic acids. Journal of Controlled Release 107(2): 276-287.
Lu, James J. et al., (2009) A Novel Mechanism Is Involved in Cationic Lipid-Mediated Functional siRNA Delivery. Mol. Pharm 6(3):763-771.
Juni, Kazuhiko et al., (1985) Modification of the release rate of aclarubicin from polylactic acid microspheres by using additives. Chem Pharm Bull (Tokyo) 33(4):1734-1738.
Khoshnoodi, Jamshid et al., (2006) Molecular recognition in the assembly of collagens: terminal noncollagenous domains are key recognition modules in the formation of triple helical protomers. J Biol Chem 281(50):38117-38121.
Martino, Sabata et al., (2009) Efficient siRNA Delivery by the Cationic Liposome DOTAP in Human Hematopoietic Stem Cells Differentiating into Dendritic Cells. Journal of Biomedicine and Biotechnology, vol. 2009, Article ID 410260, 7 pages.
Mosesson, M. W. (2005) Fibrinogen and fibrin structure and functions. J Thromb Haemost 3(8):1894-1904.
Valenick, Leyla V. et al., (2005) Fibronectin fragmentation promotes alpha4beta1 integrin-mediated contraction of a fibrin-fibronectin provisional matrix. Exp Cell Res 309(1):48-55.
International Search Report and Written Opinion of PCT/IL09/00701 issued Nov. 12, 2009, 9 pages.
International Search Report and Written Opinion of PCT/IL10/00563 issued Oct. 29, 2010, 7 pages.
International Search Report of PCT/IL11/00054 Aug. 25, 2011, 4 pages.
Requirement for Restriction/Election from U.S. Appl. No. 13/003,955, dated Mar. 30, 2012, 9 pages.
Non-Final Rejection from U.S. Appl. No. 13/003,955, dated May 24, 2012, 11 pages.
Bildirici, Lale et al., (2000) Transfection of cells by immunoporation. Nature, vol. 405, p. 298.
Capecchi, Mario R. (1980) High efficiency transformation by direct microinjection of DNA into cultured mammalian cells. Cell, vol. 22, pp. 479-488.
Gao, X. et al., (1995) Cationic liposome-mediated gene transfer. Gene Ther, vol. 2, pp. 710-722.
Thierry, Alain R. et al., (1995) Systemic gene therapy: biodistribution and long-term expression of a transgene in mice. Proc Natl Acad Sci USA, vol. 92, pp. 9742-9746.

* cited by examiner

SUSTAINED-RELEASE DRUG CARRIER COMPOSITION

CROSS REFERENCE TO RELATED APPLICATIONS

This application is a 35 U.S.C. §371 National Phase Entry Application from PCT/IL2010/000563, filed Jul. 14, 2010, and designating the United States, and claims the benefit of U.S. Provisional Application No. 61/225,289, filed Jul. 14, 2009, the entire disclosures of which are incorporated herein by reference.

FIELD OF THE INVENTION

The present invention provides compositions for extended release of an active ingredient, comprising a lipid-based matrix with a non-biodegradable polymer. The present invention also provides methods of producing the matrix compositions and methods for using the matrix compositions to provide controlled release of an active ingredient in the body of a subject in need thereof.

BACKGROUND OF THE INVENTION

Lipid based drug delivery systems are well known in the art of pharmaceutical science. Typically they are used to formulate drugs having poor bioavailability or high toxicity or both. Among the prevalent dosage forms that have gained acceptance are many different types of liposomes, including small unilamellar vesicles, multilamellar vesicles and many other types of liposomes; different types of emulsions, including water in oil emulsions, oil in water emulsions, water-in-oil-in-water double emulsions, submicron emulsions, microemulsions; micelles and many other hydrophobic drug carriers. These types of lipid based delivery systems can be highly specialized to permit targeted drug delivery or decreased toxicity or increased metabolic stability and the like. Extended release in the range of days, weeks and more are not profiles commonly associated with lipid based drug delivery systems in vivo.

Ideally sustained release drug delivery systems should exhibit kinetic and other characteristics readily controlled by the types and ratios of the specific excipients used. Advantageously the sustained release drug delivery systems should provide solutions for hydrophilic, amphipathic as well as hydrophobic drugs.

Periodontitis

The use of systemic doxycycline and NSAIDs in combination therapy has been shown to suppress tissue damage in the gingiva of chronic periodontitis patients. Tissue damage is caused by the action of pathogenic bacteria in combination with host matrix metalloproteinase (MMP) activity. Antibiotic treatment in combination with anti-inflammatory medication suppresses these two pathways. An increase in efficacy and reduction of side effects of treatment would be achieved by a means of releasing these medications locally in a controlled fashion.

Bone Augmentation

Bone diseases requiring bone augmentation include benign and malignant bone tumors, cancers situated in bones, infectious bone diseases, and other bone diseases of etiology related to endocrinology, autoimmunity, poor nutrition, genetic factors, and an imbalance between bone growth and resorption. Examples are diseases such as osteosarcoma/malignant fibrous histiocytoma of bone (PDQ), osteosarcoma, chondrosarcoma, Ewing's sarcoma, malignant fibrous histiocytoma, fibrosarcoma and malignant fibrous histiocytoma, giant cell tumor of bone, chordoma, lymphoma, multiple myeloma, osteoarthritis, Paget's disease of bone, arthritis, degenerative changes, osteoporosis, osteogenesis imperfecta, bone spurs, renal osteodystrophy, hyperparathyroidism, osteomyelitis, enchondroma, osteochondroma, osteopetrosis, bone and joint problems associated with diabetes.

Immediate and delayed infection is a major complication in the field of orthopedics. Reducing the complications after orthopedic treatment will induce the efficiency and success of the orthopedic treatment and in some cases it will reduce the mortality. There is also a need to allow treatment in infected sites and to induce the efficacy of the treatment in the infected sites.

Another important aspect in the field of orthopedics or orthopedic surgery is the need to accelerate soft and hard tissue recovery in reparative and regenerative procedures.

Bone augmentation further comprises a variety of procedures that are used to "build" bone so that implants can be placed. These procedures typically involve grafting bone or bonelike materials to the treated area (e.g. lost bone as a result of bone tumor or cancer metastasis removal) and waiting for the grafted material to fuse with the existing bone over several months. Typically, bone removal surgery for the removal of tumor is followed by chemotherapy or radiology treatment. One of the drawbacks of systemic chemotherapy is its limited ability to completely eradicate potential left-over tumor cells due to the limited blood supply in the grafted area. Furthermore, radio-therapy is limited due to the slow recovery of the injured bone. Therefore, slow and long term release of anti-cancer agents, directly in the location needed would be highly beneficial.

Liposomes and Biodegradable Polymers in Drug Delivery

To date the use of lipids in conjunction with biopolymers has been contemplated but these have not yet been introduced successfully into clinical practice.

U.S. Pat. No. 3,773,919 to Boswell et al describes the use of polymers derived from alpha-hydroxycarboxylic acids including lactic acid, glycolic acid and co-polymers thereof and their use in sustained release formulations.

Liposomes are described in U.S. Pat. No. 4,522,803 to Lenk et al. Liposomes typically exhibit adequate drug delivery drug-holding capacity but relatively limited in vivo half-lives. Many different types of liposomes have been developed for particular applications. Examples can be found in U.S. Pat. Nos. 5,043,166; 5,316,771; 5,919,480; 6,156,337; 6,162,462; 6,787,132; 7,160,554, among others.

U.S. Pat. Nos. 6,333,021 and 6,403,057 to Schneider et al disclose microcapsules having a biodegradable membrane encapsulating a gas core.

U.S. Pat. Nos. 6,277,413 and 6,793,938 to Sankaram disclose biodegradable lipid/polymer-containing compositions prepared by utilizing aqueous solutions, precluding formation of a water-resistant, lipid-saturated matrix.

U.S. Pat. No. 4,882,167 to Jang discloses a controlled release matrix for tablets or implants of biologically active agents produced by dry direct compression of a hydrophobic carbohydrate polymer, e.g. ethyl cellulose; and a difficult-to-digest soluble component, i.e. a wax, e.g. carnauba wax, a fatty acid material, or a neutral lipid.

US Patent Application 2006/0189911 to Fukuhira et al discloses an anti-adhesion membrane of a honeycomb film made of polylactic acid as a biodegradable polymer and a phospholipid.

US Patent Application 2004/0247624 discloses methods for the preparation of a pharmaceutical composition comprising an organic solvent, a drug and a stabilizing agent selected from a polymer, a lipid, a polymer-lipid conjugate or a combination thereof.

US Patent Application 2006/0073203 to Ljusberg-Wahren et al discloses an orally administrable composition comprising a dry mixture of polymer, lipid and bioactive agent, intended upon contact with water or gastrointestinal fluids to form particles comprising the lipid, the bioactive agent, and optionally also water. The polymers utilized, disintegrate in the digestive tract during the digestive process; e.g. a time period of less than one day.

International Patent Application Publication WO/2010/007623 to the inventors of the present invention provides compositions for extended release of an active ingredient, comprising a lipid-saturated matrix formed from a polyester based biodegradable polymer.

Despite the advances recently made in the art, there is an immediate need for improved compositions adapted to achieve sustained release or programmed release or controlled release from a lipid-saturated polymeric matrix for periodontal or orthopedic uses.

SUMMARY OF THE INVENTION

Embodiments of the present invention provide compositions for extended release of an active ingredient, comprising a lipid-based matrix comprising a non-biodegradable polymer. Other embodiments of the present invention provide methods of producing the matrix compositions and methods for using the matrix compositions to provide controlled release of an active ingredient in the body of a subject in need thereof.

In one aspect, the present invention provides a matrix composition comprising: (a) a pharmaceutically acceptable, biocompatible non-biodegradable polymer in association with a first lipid having a polar group; (b) a second lipid selected from phospholipids having fatty acid moieties of at least 14 carbons; and (c) a pharmaceutical active agent, where the matrix composition is adapted for providing sustained release of the pharmaceutical agent. According to some embodiments, the first lipid having a polar group comprises at least one sterol. According to some embodiments, the first lipid having a polar group is other than a phospholipid. According to some embodiments, the first lipid comprises a mixture of lipids. According to some embodiments, the first lipid comprises a mixture of lipids wherein at least one of the lipids is a sterol. According to some embodiments, the non-biodegradable polymer is not bonded to the first lipid having a polar group. According to some embodiments, the second lipid comprises a mixture of lipids, wherein at least one is a phospholipid having fatty acid moieties of at least 14 carbons According to some embodiments, the non-biodegradable polymer is not bonded to the second lipid. According to some embodiments, the non-biodegradable polymer is not bonded to the phospholipids. According to some preferable embodiments, the first lipid and the second lipid are distinct category of lipids. In specific embodiments, the polymer and the phospholipids form a matrix composition that is substantially free of water.

According to some embodiments, the non-biodegradable polymer may comprise polyethylene glycol, polyethylene glycol (PEG) acrylate, polymethacrylates (e.g. PEG methacrylate, polymethylmethacrylate, polyethylmethacrylate, polybutylmethacrylate, poly-2-ethylhexylmethacrylate, polylaurylmethacrylate, polyhydroxylethyl methacrylate), poly-methylacrylate, 2-methacryloyloxyethylphosphorylcholine (MPC), polystyrene, derivatized polystyrene, polylysine, poly N-ethyl-4-vinyl-pyridinium bromide, silicone, ethylene-vinyl acetate copolymers, polyethylenes, polypropylenes, polytetrafluoroethylenes, polyurethanes, polyacrylates, polyvinyl acetate, ethylene vinyl acetate, polyethylene, polyvinyl chloride, polyvinyl fluoride, copolymers of polymers of ethylene-vinyl acetates and acyl substituted cellulose acetates, poly(vinyl imidazole), chlorosulphonate polyolefins, polyethylene oxide, polyoxymethylene (Delrin®), polyurethane, polyamides, polypropylene, polyvinyl chloride, polymethacrylic acid, and derivatives thereof alone and mixtures thereof.

According to particular embodiment, the non-biodegradable polymer comprises polyethylene glycol having a molecular weight from about 1000 to about 20000; alternatively, between 2000 to about 10000. According to an exemplary embodiment, the polyethylene glycol has a molecular weight between about 4000 to about 8000.

In another aspect, the present invention provides a matrix composition comprising: (a) a pharmaceutically acceptable, biocompatible biodegradable polymer other than a polyester in association with a first lipid having a polar group; (b) a second lipid selected from phospholipids having fatty acid moieties of at least 14 carbons; and (c) a pharmaceutical active agent, where the matrix composition is adapted for providing sustained release of the pharmaceutical agent. In specific embodiments, the polymer and the phospholipids form a matrix composition that is substantially free of water.

According to some embodiment, the biodegradable polymer is selected from the group consisting of poly(caprolactone), polycarbonates, polyesteramides, polyanhydrides, poly(amino acid)s, polycyanoacrylates, polyamides, polyacetals, poly(ether ester)s, poly(dioxanone)s, poly(alkylene alkylate)s, biodegradable polyurethanes, blends and copolymers thereof.

According to some embodiments, the polymer may include any combination of a non-biodegradable polymer and a biodegradable polymer. According to some particular embodiments, the polymer may include any combination of a non-biodegradable polymer and a biodegradable polymer other than a polyester. According to some embodiments, the polymer may include more than one type of a non-biodegradable polymer, more than one type of a biodegradable polymer or a combination thereof.

According to some embodiments, the matrix composition further comprises a biodegradable polymer, wherein the non-biodegradable polymer and the biodegradable polymer form a block co-polymer. According to some embodiments, the block co-polymer is a linear co-polymer ((AB)n, (ABA)n or (ABABA)n wherein n≥1). According to some other embodiments, the block co-polymer is a branched co-polymer (multiple A's depending from one B). In these formulae, A is a non-biodegradable polymer and B is a biodegradable polymer; alternatively, A is a non-biodegradable polymer and B is a biodegradable polymer other than a polyester. According to some embodiments, A is a non-biodegradable polymer having a molecular weight lower than 5000 dalton; alternatively, lower than 4000 dalton; alternatively, lower than 3000 dalton; alternatively, lower than 2000 dalton. Non-limiting examples of suitable block co-polymers include PEG-PLA-PEG and PEG-PLGA-PEG. According to some embodiments, the polymer may include any combination of a non-biodegradable polymer, a biodegradable polymer and a block co-polymer as defined above. According to some embodiments, the block co-polymer comprises more than one type of non-biodegradable polymer, more than one type of biodegradable polymer or a combination thereof. Each possibility represents a separate embodiment of the present invention.

According to some embodiments, the polymer comprises non-biodegradable polymer chains having a molecular weight lower than 5000 dalton, linked to each other by a biodegradable linker. Non limiting examples of biodegradable linkers include disulfide bonds and ester bonds.

According to some embodiments the first lipid having a polar group is selected from a sterol, a tocopherol and a phosphatidylethanolamine. According to some embodiments, the first lipid having a polar group is selected from a sterol. According to particular embodiments the first lipid is mixed with the biocompatible polymer to form a non-covalent association. According to some exemplary embodiments, the first lipid having a polar group is cholesterol.

According to some embodiments the second lipid comprises a phosphatidylcholine. According to some embodiments the second lipid comprises a mixture of phosphatidylcholines. According to some embodiments the second lipid comprises a mixture of a phosphatidylcholine and a phosphatidylethanolamine, or any other types of phospholipids.

Any type of drug molecule may be incorporated into the matrix compositions for sustained and/or controlled release and/or extended release. According to particular embodiments the pharmaceutically active agent is selected from the group consisting of an antibiotic, an antifungal, an NSAID, a steroid, an anti-cancer agent, an osteogenic factor, a bone resorption inhibitor and any combination thereof. According to alternative embodiments the pharmaceutical active agent is selected from a hydrophobic agent, an amphipathic agent or a water soluble agent. Each possibility represents a separate embodiment of the present invention.

In another embodiment, the phospholipid is a phosphatidylcholine having fatty acid moieties of at least 14 carbons. In another embodiment, the composition further comprises a phosphatidylethanolamine having fatty acid moieties of at least 14 carbons. In another embodiment, the matrix composition is homogeneous. In another embodiment, the matrix composition is in the form of a lipid-based matrix whose shape and boundaries are determined by the polymer. In another embodiment, the matrix composition is in the form of an implant.

In some embodiments, the pharmaceutical active agent is an antibiotic incorporated into the matrix composition. In some embodiments, the antibiotic has low water solubility. In another embodiment, the antibiotic is a hydrophobic antibiotic. In another embodiment, the antibiotic is an amphipathic antibiotic. In another embodiment, the composition further comprises a non-steroidal anti-inflammatory drug (NSAID). In another embodiment, the NSAID as well is incorporated into the matrix composition. In another embodiment, the NSAID has low water solubility. In another embodiment the matrix composition may comprise a combination of two or more active agents. In another embodiment, the matrix composition may comprise a combination of an antibiotic and a NSAID. Each possibility represents a separate embodiment of the present invention.

In a particular embodiment, the present invention provides a matrix composition comprising: (a) non-biodegradable polymer; (b) a sterol; (c) a phosphatidylethanolamine having fatty acid moieties of at least 14 carbons; (d) a phosphatidylcholine having fatty acid moieties of at least 14 carbons; and (e) an antibiotic or antifungal agent. In another embodiment, the matrix composition comprises at least 50% lipid by weight. In another embodiment, the matrix composition is homogeneous. In another embodiment, the matrix composition is in the form of a lipid-based matrix whose shape and boundaries are determined by the polymer. In another embodiment, the matrix composition is in the form of an implant.

According to some exemplary embodiments, the present invention provides a matrix composition comprising: (a) polyethylene glycol; (b) a sterol; (c) a phosphatidylcholine having fatty acid moieties of at least 14 carbons; and (d) an antibiotic or antifungal agent. In another embodiment, the matrix composition comprises at least 30% lipid (sterol and phospholipids) by weight. In another exemplary embodiment, the sterol is cholesterol. In another embodiment, the matrix composition is homogeneous. In another embodiment, the matrix composition is in the form of a lipid-based matrix whose shape and boundaries are determined by the polymer. In another embodiment, the shape and boundaries of the matrix composition are determined by the polymer in compositions comprising at least 50% polymer by weight. In another embodiment, the matrix composition is in the form of an implant.

According to alternative embodiments the antibiotic or antifungal agent is selected from a hydrophobic agent, an amphipathic agent or a water soluble agent. Each possibility represents a separate embodiment of the present invention.

In another embodiment, the present invention provides a matrix composition comprising: (a) non-biodegradable polymer; (b) a sterol; (c) a phosphatidylethanolamine having fatty acid moieties of at least 14 carbons; (d) a phosphatidylcholine having fatty acid moieties of at least 14 carbons; and (e) a non-steroidal anti-inflammatory drug (NSAID). In another embodiment, the matrix composition comprises at least 30% lipid. In another embodiment, the NSAID has low water solubility. In another embodiment, the NSAID is a hydrophobic NSAID. In another embodiment, the NSAID is an amphipathic NSAID. In another embodiment, the matrix composition is in the form of a lipid-based matrix whose shape and boundaries are determined by the polymer. In another embodiment, the shape and boundaries of the matrix composition are determined by the polymer in compositions comprising at least 50% polymer by weight.

In another embodiment, the matrix composition is in the form of an implant. In another embodiment, the matrix composition is homogeneous. Each possibility represents a separate embodiment of the present invention.

In another embodiment, the present invention provides a matrix composition comprising: (a) non-biodegradable polymer; (b) a sterol; (c) a phosphatidylethanolamine having fatty acid moieties of at least 14 carbons; (d) a phosphatidylcholine having fatty acid moieties of at least 14 carbons; and (e) an osteogenic factor or a bone resorption inhibitor. In another embodiment, the matrix composition comprises at least 30% lipid. In another embodiment, the bone resorption inhibitor has low water solubility. In another embodiment, the bone resorption inhibitor is a hydrophobic bone resorption inhibitor. In another embodiment, the bone resorption inhibitor is an amphipathic bone resorption inhibitor. In another embodiment, the composition further comprises an NSAID. In another embodiment, the NSAID as well is incorporated into the matrix composition. In another embodiment, the matrix composition is in the form of a lipid-based matrix whose shape and boundaries are determined by the polymer. In another embodiment, the shape and boundaries of the matrix composition are determined by the polymer in compositions comprising at least 50% polymer by weight. In another embodiment, the matrix composition is in the form of an implant. In another embodiment, the matrix composition is homogeneous. Each possibility represents a separate embodiment of the present invention.

In another embodiment, the present invention provides a matrix composition comprising: (a) non-biodegradable polymer; (b) a sterol; (c) a phosphatidylethanolamine having saturated fatty acid moieties of at least 14 carbons; (d) a phosphatidylcholine having saturated fatty acid moieties of at least 14 carbons; (e) an active agent; and (f) a targeting moiety capable of interacting with a surface molecule of a target cell. In another embodiment, the active agent is selected from the group consisting of an NSAID, an antibiotic, an antifungal agent, a steroid, an anti-cancer agent, an osteogenic factor and a bone resorption inhibitor. In another embodiment, the polymer and the phospholipid form a matrix composition that is substantially free of water. In another embodiment, the matrix composition is capable of being degraded in vivo to vesicles into which some or all the mass of the released active agent is integrated. In another embodiment, the matrix composition is capable of being degraded in vivo to form vesicles into which the active agent and the targeting moiety are integrated. Each possibility represents a separate embodiment of the present invention.

In another embodiment, the present invention provides a pharmaceutical composition comprising a matrix composition of the present invention and a pharmaceutically acceptable excipient. In another embodiment, the matrix composition is in the form of microspheres. In another embodiment, the present invention provides a pharmaceutical composition comprising microspheres of the present invention and a pharmaceutically acceptable excipient. In another embodiment, the pharmaceutical composition is in a parenterally injectable form. In another embodiment, the pharmaceutical composition is in an infusible form. In another embodiment, the excipient is compatible for injection. In another embodiment, the excipient is compatible for infusion. Each possibility represents a separate embodiment of the present invention.

In another embodiment, a matrix composition of the present invention is in the form of an implant, following evaporation of the organic solvents. In another embodiment, the implant is homogeneous. Each possibility represents a separate embodiment of the present invention.

In some embodiments, the polymer of the present invention is associated with the sterol via non-covalent bonds. In some embodiments, the polymer of the present invention is associated with the sterol via hydrogen bonds.

In another embodiment, the process of creating an implant from a composition of the present invention comprises the steps of (a) creating a matrix composition according to a method of the present invention in the form of a bulk material; and (b) transferring the bulk material into a mold or solid receptacle of a desired shape.

Also provided herein are methods for making the compositions of the invention and methods of use thereof.

According to another aspect a matrix composition for sustained release of a pharmaceutical agent is generated by a process comprising: providing a first solution or dispersion of a volatile organic solvent comprising a biocompatible polymer selected from the group consisting of a non-biodegradable polymer, a biodegradable polymer other than polyester or a combination thereof, and a first lipid having a polar group; providing a second solution or dispersion comprising a second volatile organic solvent and a second lipid, the second lipid comprising at least one phospholipid, and a pharmaceutical active agent; mixing the first and second solutions to form a homogeneous mixture; evaporating the volatile solvents to produce a homogeneous polymer phospholipid matrix comprising a pharmaceutical active agent. The selection of the specific solvents is made according to the specific drug and other substances used in the particular formulation intended to entrap a specific active and to release it in a specific pre-planned rate and duration. The evaporation is conducted at controlled temperature determined according to the properties of the solution obtained. According to some embodiments, the volatile organic solvents used in methods of the invention had a freezing temperature lower than 0° C.; alternatively, lower than 10° C.; alternatively, lower than 20° C.

According to the present disclosure the use of different types of volatile organic solutions, and the absence of water throughout the process, enable the formation of homogeneous water-resistant, lipid based matrix compositions. According to various embodiments the first and second solvents can be the same or different. According to some embodiments one solvent can be non-polar and the other preferably water-miscible.

In another embodiment, the matrix composition of methods and compositions of the present invention is substantially free of water. "Substantially free of water" refers, in another embodiment, to a composition containing less than 1% water by weight. In another embodiment, the term refers to a composition containing less than 0.8% water by weight. In another embodiment, the term refers to a composition containing less than 0.6% water by weight. In another embodiment, the term refers to a composition containing less than 0.4% water by weight. In another embodiment, the term refers to a composition containing less than 0.2% water by weight. In another embodiment, the term refers to the absence of amounts of water that affect the water-resistant properties of the composition. In another embodiment, the term refers to a composition manufactured without the use of any aqueous solvents. In another embodiment, producing the composition using a process substantially free of water, as described herein, enables lipid saturation. Lipid saturation confers upon the matrix composition ability to resist bulk degradation in vivo; thus, the matrix composition exhibits the ability to mediate extended release on a scale of several days, weeks or months.

In another embodiment, the matrix composition is essentially free of water. "Essentially free" refers to a composition comprising less than 0.1% water by weight. In another embodiment, the term refers to a composition comprising less than 0.08% water by weight. In another embodiment, the term refers to a composition comprising less than 0.06% water by weight. In another embodiment, the term refers to a composition comprising less than 0.04% water by weight. In another embodiment, the term refers to a composition comprising less than 0.02% water by weight. In another embodiment, the term refers to a composition comprising less than 0.01% water by weight. Each possibility represents a separate embodiment of the present invention.

In another embodiment, the matrix composition is free of water. In another embodiment, the term refers to a composition not containing detectable amounts of water. Each possibility represents a separate embodiment of the present invention.

In another embodiment, the present invention provides a method of producing a matrix composition, the method comprising the steps of (a) combining with a non-polar, volatile organic solvent: (i) a non-biodegradable polymer, a biodegradable polymer other than polyester or a combination thereof and (ii) a sterol; (b) combining with a water-miscible, volatile organic solvent: (i) an active agent selected from the group consisting of a non-steroidal anti-inflammatory drug (NSAID), an antibiotic, an antifungal a steroid, an anti-cancer agent, and osteogenic factor, a bone resorption inhibitor and any combination thereof; (ii) a phosphatidylethanolamine;

and (iii) a phosphatidylcholine; and (c) mixing and homogenizing the products resulting from steps (a) and (b). In another embodiment, the phosphatidylethanolamine is included in the non-polar, volatile organic solvent instead of the water-miscible, volatile organic solvent. In another embodiment, the non-biodegradable polymer is selected from the group consisting of polyethylene glycol, polyethylene glycol (PEG) acrylate, polymethacrylates (e.g. PEG methacrylate, polymethylmethacrylate, polyethylmethacrylate, polybutylmethacrylate, poly-2-ethylhexylmethacrylate, polylaurylmethacrylate, polyhydroxylethyl methacrylate), poly-methylacrylate, 2-methacryloyloxyethylphosphorylcholine (MPC), polystyrene, derivatized polystyrene, polylysine, poly N-ethyl-4-vinyl-pyridinium bromide, silicone, ethylene-vinyl acetate copolymers, polyethylenes, polypropylenes, polytetrafluoroethylenes, polyurethanes, polyacrylates, polyvinyl acetate, ethylene vinyl acetate, polyethylene, polyvinyl chloride, polyvinyl fluoride, copolymers of polymers of ethylene-vinyl acetates and acyl substituted cellulose acetates, poly(vinyl imidazole), chlorosulphonate polyolefins, polyethylene oxide, and mixtures thereof. In another embodiment, the non-biodegradable polymer is any other suitable non-biodegradable polymer known in the art. In another embodiment, the mixture containing the non-polar, organic solvent is homogenized prior to mixing it with the mixture organic solvent. In another embodiment, the mixture containing the water-miscible, organic solvent is homogenized prior to mixing it with the mixture containing the non-polar, organic solvent. In another embodiment, the polymer in the mixture of step (a) is lipid saturated. In another embodiment, the matrix composition is lipid saturated. Each possibility represents a separate embodiment of the present invention.

In another embodiment, the matrix composition of the present invention can be used for coating fully or partially the surface of different substrates. In another embodiment substrates to be coated include at least one material selected from the group consisting of carbon fibers, stainless steel, cobalt-chromium, titanium alloy, tantalum, ceramic and collagen or gelatin. In another embodiment substrates may include any medical devices such as orthopedic nails, orthopedic screws, orthopedic staples, orthopedic wires and orthopedic pins used in orthopedic surgery, metal or polymeric implants used in both orthopedic and periodontal surgery, bone filler particles and absorbable gelatin sponge. Bone filler particles can be any one of allogeneic (i.e., from human sources), xenogeneic (i.e., from animal sources) and artificial bone particles. In another embodiment a treatment using the coated substrates and administration of the coated substrates will follow procedures known in the art for treatment and administration of similar uncoated substrates. In another embodiment bone filler particles coated with the matrix of the present invention are administered substantially as a single ingredient (not administered as part of a mixture with other ingredients). Alternatively, the coated bone filler particles are mixed with any other commercially available bone filler particles or autologous bone before administration. In another embodiment, the mixture of bone filler particles comprises at least one of: non-coated particles, particles coated with matrix compositions incorporating a pharmaceutically active agent, particles coated with matrix compositions incorporating a plurality of pharmaceutically active agents or a combination thereof. In another embodiment the amounts, ratios and types of ingredients forming the matrix composition of the present invention are varied so to adjust the polymer-lipid basis to the biophysical/biochemical properties of the pharmaceutically active agent, the therapeutically effective dose of the pharmaceutically active agent and to the desired sustained release time period (typically in the range of days to months). In another embodiment bone filler particles coated with matrix composition comprising an active agent are mixed with bone filler particles coated with matrix composition comprising a different active agent before administration. It is to be emphasized that within the scope of the present invention are bone particles coated with different matrix compositions comprising different active agents, compositions comprising different lipid/polymer ratio, compositions comprising different lipid content or any combination thereof. Such mixtures may be used for combination treatment in which the release rate of each of the active agents is separately controlled.

It is to be emphasized that the sustained release period using the compositions of the present invention can be programmed taking into account two major factors: (i) the weight ratio between the polymer and the lipid content, specifically the phospholipid having fatty acid moieties of at least 14 carbons, and (ii) the biochemical and/or biophysical properties of the polymer and the lipid. Specifically, the fluidity of the lipid should be considered. For example, a phosphatidylcholine (14:0) is more fluid (less rigid and less ordered) at body temperature than a phosphatidylcholine (18:0). Thus, for example, the release rate of a drug incorporated in a matrix composition comprising PEG 8000 and phosphatidylcholine (18:0) will be slower than that of a drug incorporated in a matrix composed of PEG 8000 and phosphatidylcholine (14:0).

When the polymer used in the matrix composition comprises polymer units having a molecular weight of up to 5000 dalton linked by a biodegradable linker, the nature of the biodegradable linker may influence the release period of the active agent entrapped/encapsulated in the composition. Alternatively, when the polymer comprises a block co-polymer according to embodiments of the invention, the nature of the biodegradable polymer units of the block co-polymer may influence the release period of the active agent entrapped/encapsulated in the composition. Another aspect that will determine the release rate is the physical characteristics of the entrapped or impregnated drug. In addition, the release rate of drugs can further be controlled by the addition of other lipids into the formulation of the second solution. This can includes fatty acids of different length such as lauric acid (12:0), membrane active sterols (such as cholesterol) or other phospholipids such as phosphatidylethanolamine. According to various embodiments the active agent is released from the composition over a desired period ranging between several days to several months.

These and other features and advantages of the present invention will become more readily understood and appreciated from the detailed description of the invention that follows.

DETAILED DESCRIPTION OF THE INVENTION

Figure 1A:
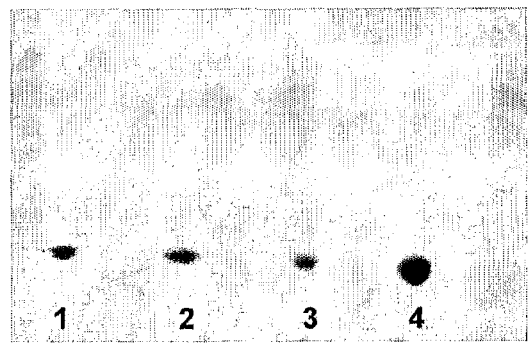
FIG. 1: A) TLC runs of extracted cholesterol (CH) from different matrix compositions; 1: PEG+CH+doxycycline hyclate (Doxy-H); 2: PEG+CH+Doxy-H+DMPC; 3: PEG+CH+Doxy-H+DSPC; 4: CH only (control); B) TLC runs of extracted phospholipids (DPPC) from PEG+CH+Doxy-H+DPPC matrix composition.
Figure 1B:
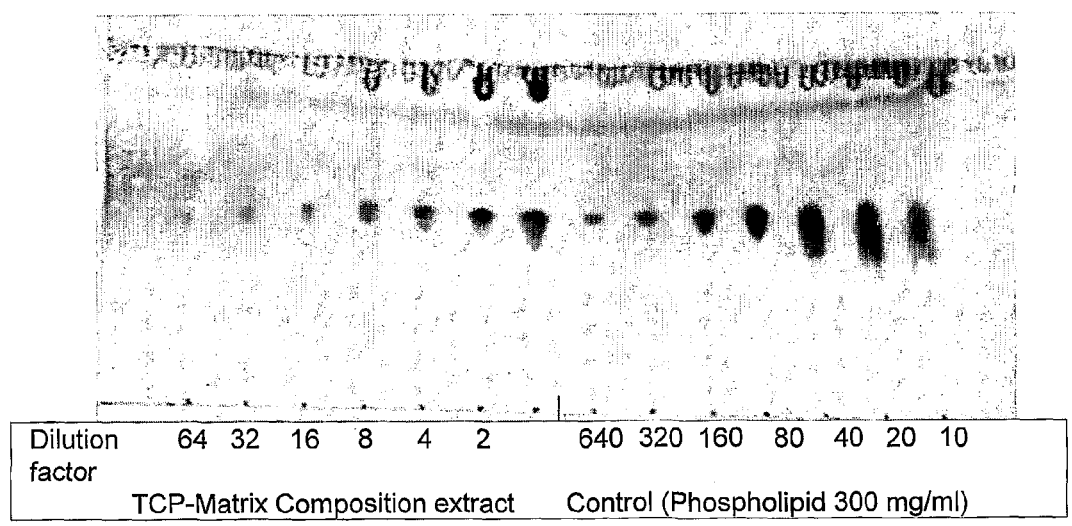

Embodiments of the present invention provides compositions for extended release of an active ingredient, comprising a lipid-based matrix comprising a non-biodegradable polymer, a biodegradable polymer which is other than polyester, a block-co-polymers of biodegradable and non biodegradable polymers or a combination thereof. The present invention also provides methods of producing the matrix compositions and methods for using the matrix compositions to provide controlled release of an active ingredient in the body of a subject in need thereof.

The matrix composition according to the embodiments of the present invention display many advantages over known in the art matrix composition comprising biodegradable polymers. Matrix composition comprising non-biodegradable polymers are inert. As such they are less prone to interference with the surrounding environment and influence tissue functions. Typically, non-biodegradable polymers are hypoallergenic and do not interfere with the activity of the immune system. Furthermore, the sub structure of non-biodegradable polymers is stable and cannot be further metabolized by bacteria and/or fungi in contrast to the degradation products of biodegradable polymers.

Another advantage of using non-biodegradable polymers in the matrix compositions of the invention relates to the drug entrapped/encapsulates within the matrix. When using biodegradable polymers, the physical environment within the matrix composition and in close proximity to the matrix composition may alter due to the degradation of the polymers; for example: PLGA, PLA and PLG may elevate the local acidity due to the release of lactic acid and/or glycolic acid monomers. This may be crucial when the entrapped or encapsulated drug is pH sensitive (e.g. polypeptides and protein based drugs).

Matrix composition comprising non-biodegradable polymers, specifically non-biodegradable polymers having a molecular weight above 5000 dalton, may serve as a permanent/long term physical backbone support to the lipidic component, supporting the overall structure of an implant or another medical device coated with the matrix composition during as well as after the release of the drug and the lipids.

Other advantages of using matrix formulations comprising non-biodegradable compositions include: a) Cost: some of the non-biodegradable polymers such as PEG, are relatively cheap compared to polyesters; b) Elimination: low molecular non-biodegradable polymers such as PEG (MW≤5 KD) are easily eliminated from the body through the urine; c) Easy to work with: Non-biodegradable polymers are less sensitive to the physical/chemical conditions (e.g. temp, pH) required during preparation.

The term "controlled release" refers to control of the rate and/or quantity of pharmaceutically active agent(s) delivered by the matrix compositions of the invention. The controlled release can be continuous or discontinuous, and/or linear or non-linear.

The term "sustained release" means that the active agent or drug is released at a rate that is significantly slower than the release expected due to diffusion under the same physical and chemical conditions. As used herein sustained release means that the release profile will provide a local therapeutically effective concentration over a period of days or weeks or months. The systemic concentrations may be significantly lower than the local concentrations of release from the matrix to the desired site of action, thereby achieving decreased toxicity as well as prolonged therapeutic effectiveness.

In certain embodiments, the present invention provides a matrix composition comprising: (a) non-biodegradable polymer; (b) a phosphoglyceride having hydrocarbon moieties of at least 14 carbons; and (c) a pharmaceutical active agent. According to some embodiments the pharmaceutical agent is selected from the group consisting of an antibiotic, an anti-fungal, an NSAID, a steroid, an anticancer agent, an osteogenic factor and a bone resorption inhibitor.

In certain embodiments the phosphoglyceride is a phospholipid. In some embodiments, the phospholipid is a phosphatidylcholine having fatty acid moieties of at least 14 carbons. In another embodiment, the composition further comprises a phosphatidylethanolamine having a fatty acid moiety of at least 14 carbons. In another embodiment, the composition further comprises a sterol. In some embodiments the sterol is cholesterol.

In another embodiment, the matrix composition is lipid saturated. "Lipid saturated," as used herein, refers to saturation of the polymer of the matrix composition with lipids including phospholipids, in combination with any hydrophobic drug and targeting moiety present in the matrix, and any other lipids that may be present. The matrix composition is saturated by whatever lipids are present. Lipid-saturated matrices of the present invention exhibit the additional advantage of not requiring a synthetic emulsifier or surfactant such as polyvinyl alcohol; thus, compositions of the present invention are typically substantially free of polyvinyl alcohol. Methods for determining the polymer:lipid ratio to attain lipid saturation and methods of determining the degree of lipid saturation of a matrix are described herein below.

In another embodiment, the matrix composition is homogeneous. In another embodiment, the matrix composition is in the form of a lipid-saturated matrix whose shape and boundaries are determined by the polymer. In another embodiment, the matrix composition is in the form of an implant. Preferably, the non-biocompatible polymer, the phosphatidylethanolamine, and the sterol are incorporated into the matrix composition. In another embodiment, the phosphatidylcholine is also incorporated into the matrix composition. In another embodiment, the antibiotic is also incorporated into the matrix composition. In another embodiment, the antibiotic has low water solubility. In another embodiment, the antibiotic is a hydrophobic antibiotic. In another embodiment, the antibiotic is an amphipathic antibiotic. In another embodiment, the composition further comprises a non-steroidal anti-inflammatory drug (NSAID). In another embodiment, the NSAID as well is incorporated into the matrix composition. In another embodiment, the NSAID has low water solubility. Each possibility represents a separate embodiment of the present invention.

In one embodiment, the present invention provides a matrix composition comprising: (a) a non-biodegradable polymer (b) a sterol; (c) a phosphatidylethanolamine having a fatty acid moiety of at least 14 carbons; (d) a phosphatidylcholine having a fatty acid moiety of at least 14 carbons; and (e) an antibiotic or an antifungal. In another embodiment, the matrix composition is lipid saturated. Preferably, the polymer, the phosphatidylethanolamine, and the sterol are incorporated into the matrix composition. In another embodiment, the phosphatidylcholine is also incorporated into the matrix composition. In another embodiment, the antibiotic is also incorporated into the matrix composition. In another embodiment, the antibiotic has low water solubility. In another embodiment, the antibiotic is a hydrophobic antibiotic. In another embodiment, the antibiotic is an amphipathic antibiotic. In another embodiment, the composition further comprises a non-steroidal anti-inflammatory drug (NSAID). In another embodiment, the NSAID as well is incorporated into the matrix composition. In another embodiment, the NSAID has low water solubility. In another embodiment, the matrix composition is in the form of a lipid-saturated matrix whose shape and boundaries are influenced by the nature of the polymer. In another embodiment, the matrix composition is in the form of an implant. In another embodiment, the matrix composition is homogeneous. Each possibility represents a separate embodiment of the present invention.

In another embodiment, the present invention provides a matrix composition comprising: (a) non-biodegradable polymer; (b) a sterol; (c) a phosphatidylethanolamine having fatty acid moieties of at least 14 carbons; (d) a phosphatidylcholine having fatty acid moieties of at least 14 carbons; (e) a non-steroidal anti-inflammatory drug (NSAID). In another embodiment, the matrix composition is lipid saturated. Preferably, the polyester, the phosphatidylethanolamine, and the sterol are incorporated into the matrix composition. In another embodiment, the phosphatidylcholine is also incorporated into the matrix composition. In another embodiment, the NSAID is also incorporated into the matrix composition. In another embodiment, the NSAID has low water solubility. In another embodiment, the NSAID is a hydrophobic NSAID. In another embodiment, the NSAID is an amphipathic NSAID. In another embodiment, the matrix composition is in the form of a lipid-saturated matrix whose shape and boundaries are determined by the polymer. In another embodiment, the matrix composition is in the form of an implant. In another embodiment, the matrix composition is homogeneous. Each possibility represents a separate embodiment of the present invention.

In another embodiment, the present invention provides a matrix composition comprising: (a) non-biodegradable polymer; (b) a sterol; (c) a phosphatidylethanolamine having fatty acid moieties of at least 14 carbons; (d) a phosphatidylcholine having fatty acid moieties of at least 14 carbons; and (e) an osteogenic factor or a bone resorption inhibitor. In another embodiment, the matrix composition is lipid saturated. Preferably, the polymer, the phosphatidylethanolamine, and the sterol are incorporated into the matrix composition. In another embodiment, the phosphatidylcholine is also incorporated into the matrix composition. In another embodiment, the bone resorption inhibitor is also incorporated into the matrix composition. In another embodiment, the bone resorption inhibitor has low water solubility. In another embodiment, the bone resorption inhibitor is a hydrophobic bone resorption inhibitor. In another embodiment, the bone resorption inhibitor is an amphipathic bone resorption inhibitor. In another embodiment, the composition further comprises an NSAID. In another embodiment, the NSAID as well is incorporated into the matrix composition. In another embodiment, the matrix composition is in the form of a lipid-saturated matrix whose shape and boundaries are determined by the polymer. In another embodiment, the matrix composition is in the form of an implant. In another embodiment, the matrix composition is homogeneous. Each possibility represents a separate embodiment of the present invention.

In another embodiment, the present invention provides a matrix composition comprising: (a) non-biodegradable polymer; (b) a sterol; (c) a phosphatidylethanolamine having fatty acid moieties of at least 14 carbons; (d) a phosphatidylcholine having fatty acid moieties of at least 14 carbons; (e) an active agent; and (f) a targeting moiety capable of interacting with a surface molecule of a target cell, a target molecule or a target surface. In another embodiment, the matrix composition is lipid saturated. In another embodiment, the active agent is selected from the group consisting of an NSAID, an antibiotic, and a bone resorption inhibitor. In another embodiment, the polymer and the phospholipid form the matrix composition that is substantially free of water. In another embodiment, the active agent and the targeting moiety are integrated into the lipid vesicle. In another embodiment, the matrix composition is in the form of a lipid-saturated matrix whose shape and boundaries are determined by the polymer. In another embodiment, the matrix composition is in the form of an implant. In another embodiment, the matrix composition is homogeneous. Each possibility represents a separate embodiment of the present invention.

In another embodiment, the polymer of methods and compositions of the present invention is associated with the sterol via hydrogen bonds.

As provided herein, the matrix composition of methods and compositions of the present invention is capable of being molded into three-dimensional configurations of varying thickness and shape. Accordingly, the matrix formed can be produced to assume a specific shape including a sphere, cube, rod, tube, sheet, or into strings. In the case of freeze-drying, the shape is determined by the shape of a mold or support which may be made of any inert material and may be in contact with the matrix on all sides, as for a sphere or cube, or on a limited number of sides as for a sheet. The matrix may be shaped in the form of body cavities as required for implant design. Removing portions of the matrix with scissors, a scalpel, a laser beam or any other cutting instrument can create any refinements required in the three-dimensional structure. Each possibility represents a separate embodiment of the present invention.

Advantageously, the matrix compositions of the present invention are prepared by methods which do not involve the formation of emulsions, and may avoid the use of aqueous media altogether. The generation of emulsions that are subsequently dried necessarily results in vesicles or microspheres. In contrast, the matrices produced without aqueous media form homogeneous liquid mixtures that can be molded or formed into three dimensional articles of any shape or can coat the surface of different substrates. In order to produce molded or coated articles the mixture of polymer and lipids and active ingredients within the appropriate selected volatile organic solvents will be used to coat the desired surface or to fit the desired shape.

The matrix composition of methods and compositions of the present invention is capable of coating the surface of different substrates. Substrates to be coated include materials selected from the group consisting of carbon fibers, stainless steel, cobalt-chromium, titanium alloy, tantalum, ceramic and collagen or gelatin. Specifically, substrates may include any medical devices such as orthopedic nails, orthopedic screws, orthopedic staples, orthopedic wires and orthopedic pins used in orthopedic surgery, metal or polymeric implants used in both orthopedic and periodontal surgery, bone filler particles and absorbable gelatin sponge. Bone filler particles can be selected from any one of allogeneic (i.e., from human sources), xenogeneic (i.e., from animal sources) and artificial bone particles.

According to some embodiments, the matrix composition of the present invention is useful as a bone graft material. This term refers to a natural or synthetic material that supports attachment of new osteoblasts and osteoprogenitor cells or can induce non-differentiated stem cells or osteoprogenitor cells to differentiate into osteoblasts. In another embodiment, the bone graft material is selected from the group consisting of an allograft, an alloplast, a xenograft, and an autologous bone graft. In other example the lipid matrix of the present invention can also be used in conjunction with a collagen membrane or collagen sponge or gelatin sponge or the like.

Lipids

"Phospholipids" are phosphoglycerides having a single phosphatidyl linkage on a glycerol backbone and fatty acids at the remaining two positions. However, it is to be understood explicitly that phosphoglycerides having hydrocarbon chains other than fatty acid residues including alkyl chains, alkenyl chains or any other hydrocarbon chain of at least 14 carbons are included within the scope of the present invention. The linkage may be an ether linkage instead of an acyl linkage found in phospholipids.

"Phosphatidylcholine" refers to a phosphoglyceride having a phosphorylcholine head group. Phosphatidylcholine compounds, in another embodiment, have the following structure:

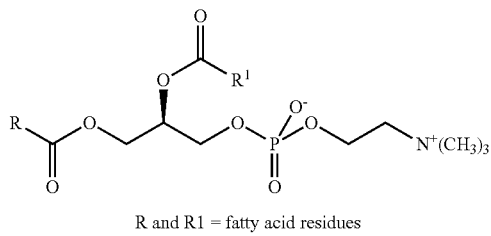

R and R1 = fatty acid residues

The R and R' moieties are fatty acids, typically naturally occurring fatty acids or derivatives of naturally occurring fatty acids. In some embodiments, the fatty acid moieties are saturated fatty acid moieties. In some embodiments, the fatty acid moieties are unsaturated fatty acid moieties. "Saturated", refers to the absence of a double bond in the hydrocarbon chain. In another embodiment, the fatty acid moieties have at least 14 carbon atoms. In another embodiment, the fatty acid moieties have 16 carbon atoms. In another embodiment, the fatty acid moieties have 18 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are palmitoyl and stearoyl. In another embodiment, the fatty acid moieties are palmitoyl and arachidoyl. In another embodiment, the fatty acid moieties are arachidoyl and stearoyl. Each possibility represents a separate embodiment of the present invention.

In another embodiment, the phosphatidylcholine is a naturally-occurring phosphatidylcholine. In another embodiment, the phosphatidylcholine is a synthetic phosphatidylcholine. In another embodiment, the phosphatidylcholine contains a naturally-occurring distribution of isotopes. In another embodiment, the phosphatidylcholine is a deuterated phosphatidylcholine. In another embodiment, the phosphatidylcholine is labeled with any other isotope or label. Preferably, the phosphatidylcholine is a symmetric phosphatidylcholine (i.e. a phosphatidylcholine wherein the two fatty acid moieties are identical). In another embodiment, the phosphatidylcholine is an asymmetric phosphatidylcholine.

Non-limiting examples of phosphatidylcholines are 1,2-distearoyl-sn-glycero-3-phosphocholine (DSPC), dioleoyl-phosphatidylcholine (DOPC), 1-palmitoyl-2-oleoyl-phosphatidylcholine, and phosphatidylcholines modified with any of the fatty acid moieties enumerated hereinabove. In another embodiment, the phosphatidylcholine is selected from the group consisting of DSPC and DOPC, and 1-palmitoyl-2-oleoyl-phosphatidylcholine.

In another embodiment, the phosphatidylcholine is any other phosphatidylcholine known in the art. Each phosphatidylcholine represents a separate embodiment of the present invention.

"Phosphatidylethanolamine" refers to a phosphoglyceride having a phosphoryl ethanolamine head group. Phosphatidylethanolamine compounds, in another embodiment, have the following structure:

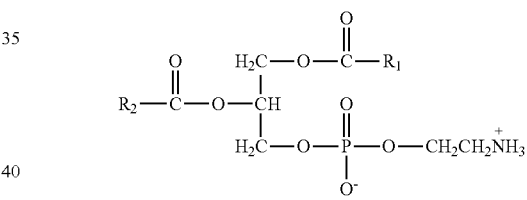

The $R_1$ and $R_2$ moieties are fatty acids, typically naturally occurring fatty acids or derivatives of naturally occurring fatty acids. In another embodiment, the fatty acid moieties are saturated fatty acid moieties. "Saturated" in another embodiment, refers to the absence of a double bond in the hydrocarbon chain. In another embodiment, the fatty acid moieties have at least 14 carbon atoms. In another embodiment, the fatty acid moieties have at least 16 carbon atoms. In another embodiment, the fatty acid moieties have 14 carbon atoms. In another embodiment, the fatty acid moieties have 16 carbon atoms. In another embodiment, the fatty acid moieties have 18 carbon atoms. In another embodiment, the fatty acid moieties have 14-18 carbon atoms. In another embodiment, the fatty acid moieties have 14-16 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are myristoyl and arachidoyl. In another embodiment, the fatty acid moieties are myristoyl and palmitoyl. In another embodiment, the fatty acid moieties are palmitoyl and stearoyl. In another embodiment, the fatty acid moieties are palmitoyl and arachidoyl. In another embodiment, the fatty acid moieties are arachidoyl and stearoyl. Each possibility represents a separate embodiment of the present invention.

In another embodiment, the phosphatidylethanolamine is a naturally-occurring phosphatidylethanolamine. In another embodiment, the phosphatidylethanolamine is a synthetic phosphatidylethanolamine. In another embodiment, the phosphatidylethanolamine is a deuterated phosphatidylethanolamine. In another embodiment, the phosphatidylethanolamine is labeled with any other isotope or label. In another embodiment, the phosphatidylethanolamine contains a naturally-occurring distribution of isotopes. Preferably, the phosphatidylethanolamine is a symmetric phosphatidylethanolamine. In another embodiment, the phosphatidylethanolamine is an asymmetric phosphatidylethanolamine.

Non-limiting examples of phosphatidylethanolamines are dimethyl dimyristoyl phosphatidylethanolamine (DMPE) and dipalmitoyl-phosphatidylethanolamine (DPPE), and phosphatidylethanolamines modified with any of the fatty acid moieties enumerated hereinabove. In another embodiment, the phosphatidylethanolamine is selected from the group consisting of DMPE and DPPE.

In another embodiment, the phosphatidylethanolamine is any other phosphatidylethanolamine known in the art. Each phosphatidylethanolamine represents a separate embodiment of the present invention.

"Sterol" in one embodiment refers to a steroid with a hydroxyl group at the 3-position of the A-ring. In another embodiment, the term refers to a steroid having the following structure:

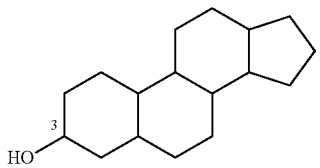

In another embodiment, the sterol of methods and compositions of the present invention is a zoosterol. In another embodiment, the sterol is cholesterol:

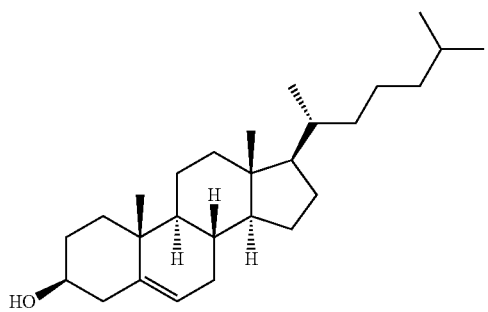

In another embodiment, the sterol is any other zoosterol known in the art. In another embodiment, the moles of sterol are up to 40% of the moles of total lipids present. In another embodiment, the sterol is incorporated into the matrix composition. Each possibility represents a separate embodiment of the present invention.

In another embodiment, the cholesterol is present in an amount of 10-50 percentage of the total weight of lipid content of the matrix composition. In another embodiment, the weight percentage is 20-50%. In another embodiment, the weight percentage is 10-40%. In another embodiment, the weight percentage is 30-50%. In another embodiment, the weight percentage is 20-60%. In another embodiment, the weight percentage is 25-55%. In another embodiment, the weight percentage is 35-55%. In another embodiment, the weight percentage is 30-60%. In another embodiment, the weight percentage is 30-55%. In another embodiment, the weight percentage is 20-50%. In another embodiment, the weight percentage is 25-55%. Each possibility represents a separate embodiment of the present invention.

In another embodiment, a composition of the present invention further comprises a lipid other than phosphatidylcholine, phosphatidylethanolamine, or a sterol. In another embodiment, the additional lipid is a phosphoglyceride. In another embodiment, the additional lipid is selected from the group consisting of a phosphatidylserine, a phosphatidylglycerol, and a phosphatidylinositol. In another embodiment, the additional lipid is selected from the group consisting of a phosphatidylserine, a phosphatidylglycerol, a phosphatidylinositol, and a sphingomyelin. In another embodiment, a combination of any 2 or more of the above additional lipids is present. In another embodiment, the polymer, phosphatidylcholine, phosphatidylethanolamine, sterol, and additional lipid(s) are all incorporated into the matrix composition. Each possibility represents a separate embodiment of the present invention.

In another embodiment, phosphatidylcholine(s) (PC) compose at least 30% of the total lipid content of the matrix composition. In another embodiment, PC(s) compose at least 35% of the total lipid content. In another embodiment, PC(s) compose at least 40% of the total lipid content. In another embodiment, PC(s) compose at least 45% of the total lipid content. In another embodiment, PC(s) compose at least 50% of the total lipid content. In another embodiment, PC(s) compose at least 55% of the total lipid content. In another embodiment, PC(s) compose at least 60% of the total lipid content. In another embodiment, PC(s) compose at least 65% of the total lipid content. In another embodiment, PC(s) compose at least 70% of the total lipid content. In another embodiment, PC(s) compose at least 75% of the total lipid content. In another embodiment, PC(s) compose at least 80% of the total lipid content. In another embodiment, PC(s) compose at least 85% of the total lipid content. In another embodiment, PC(s) compose at least 90% of the total lipid content. In another embodiment, PC(s) compose at least 95% of the total lipid content. In another embodiment, PC(s) compose over 95% of the total lipid content. Each possibility represents a separate embodiment of the present invention.

In another embodiment, a composition of the present invention further comprises a phosphatidylserine. "Phosphatidylserine" refers to a phosphoglyceride having a phosphorylserine head group. Phosphatidylserine compounds, in another embodiment, have the following structure:

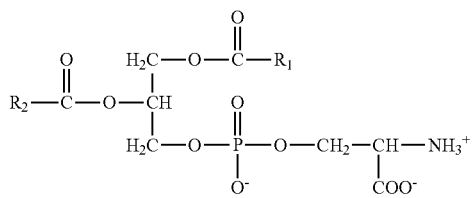

The $R_1$ and $R_2$ moieties are fatty acids, typically naturally occurring fatty acids or derivatives of naturally occurring fatty acids. In another embodiment, the fatty acid moieties are saturated fatty acid moieties. In another embodiment, the fatty acid moieties have at least 14 carbon atoms. In another embodiment, the fatty acid moieties have at least 16 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are a combination of two of the above fatty acid moieties.

In another embodiment, the phosphatidylserine is a naturally-occurring phosphatidyl serine. In another embodiment, the phosphatidylserine is a synthetic phosphatidyl serine. In another embodiment, the phosphatidylserine is a deuterated phosphatidyl serine. In another embodiment, the phosphatidylserine is labeled with any other isotope or label. In another embodiment, the phosphatidylserine contains a naturally-occurring distribution of isotopes. In another embodiment, the phosphatidylserine is a symmetric phosphatidylserine. In another embodiment, the phosphatidylserine is an asymmetric phosphatidylserine.

Non-limiting examples of phosphatidylserines are phosphatidylserines modified with any of the fatty acid moieties enumerated hereinabove. In another embodiment, the phosphatidylserine is any other phosphatidylserine known in the art. Each phosphatidylserine represents a separate embodiment of the present invention.

In another embodiment, a composition of the present invention further comprises a phosphatidylglycerol. "Phosphatidylglycerol" refers to a phosphoglyceride having a phosphoryl glycerol head group. Phosphatidylglycerol compounds, in another embodiment, have the following structure:

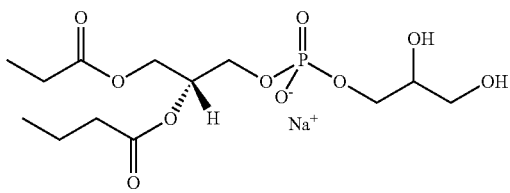 [SMILES: CCCC(=O)O[C@H](COC(=O)CC)COP(=O)([O-])OCC(O)CO ; [Na+]]

The 2 bonds to the left are connected to fatty acids, typically naturally occurring fatty acids or derivatives of naturally occurring fatty acids. In another embodiment, the phosphatidylglycerol is a naturally-occurring phosphatidylglycerol. In another embodiment, the phosphatidylglycerol is a synthetic phosphatidyl glycerol. In another embodiment, the phosphatidylglycerol is a deuterated phosphatidylglycerol. In another embodiment, the phosphatidylglycerol is labeled with any other isotope or label. In another embodiment, the phosphatidylglycerol contains a naturally-occurring distribution of isotopes. In another embodiment, the phosphatidylglycerol is a symmetric phosphatidylglycerol. In another embodiment, the phosphatidylglycerol is an asymmetric phosphatidylglycerol. In another embodiment, the term includes diphosphatidylglycerol compounds having the following structure:

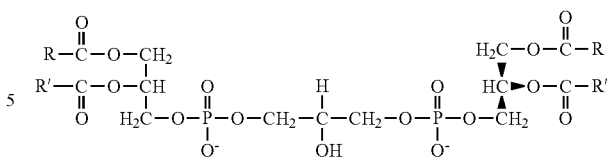

The R and R' moieties are fatty acids, typically naturally occurring fatty acids or derivatives of naturally occurring fatty acids. In another embodiment, the fatty acid moieties are saturated fatty acid moieties. In another embodiment, the fatty acid moieties have at least 14 carbon atoms. In another embodiment, the fatty acid moieties have at least 16 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are a combination of two of the above fatty acid moieties.

Non-limiting examples of phosphatidylglycerols are phosphatidylglycerols modified with any of the fatty acid moieties enumerated hereinabove. In another embodiment, the phosphatidylglycerol is any other phosphatidylglycerol known in the art. Each phosphatidylglycerol represents a separate embodiment of the present invention.

In another embodiment, a composition of the present invention further comprises a phosphatidylinositol. "Phosphatidyl inositol" refers to a phosphoglyceride having a phosphorylinositol head group. Phosphatidylinositol compounds, in another embodiment, have the following structure:

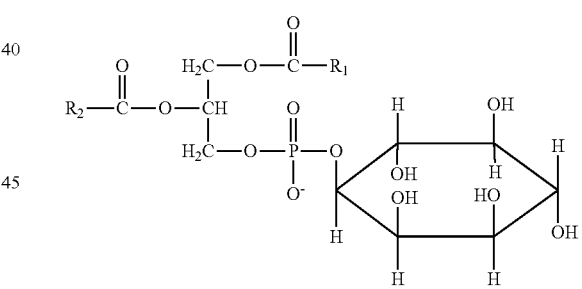

The $R_1$ and $R_2$ moieties are fatty acids, typically naturally occurring fatty acids or derivatives of naturally occurring fatty acids. In another embodiment, the fatty acid moieties are saturated fatty acid moieties. In another embodiment, the fatty acid moieties have at least 14 carbon atoms. In another embodiment, the fatty acid moieties have at least 16 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are a combination of two of the above fatty acid moieties.

In another embodiment, the phosphatidyl inositol is a naturally-occurring phosphatidylinositol. In another embodiment, the phosphatidylinositol is a synthetic phosphatidylinositol. In another embodiment, the phosphatidylinositol is a deuterated phosphatidylinositol. In another embodiment, the phosphatidylinositol is labeled with any other isotope or label. In another embodiment, the phosphatidylinositol contains a naturally-occurring distribution of isotopes. In another embodiment, the phosphatidylinositol is a symmetric phosphatidylinositol. In another embodiment, the phosphatidylinositol is an asymmetric phosphatidylinositol.

Non-limiting examples of phosphatidylinositols are phosphatidylinositols modified with any of the fatty acid moieties enumerated hereinabove. In another embodiment, the phosphatidylinositol is any other phosphatidylinositol known in the art. Each phosphatidylinositol represents a separate embodiment of the present invention.

In another embodiment, a composition of the present invention further comprises a sphingolipid. In another embodiment, the sphingolipid is ceramide. In another embodiment, the sphingolipid is a sphingomyelin. "Sphingomyelin" refers to a sphingosine-derived phospholipid. Sphingomyelin compounds, in another embodiment, have the following structure:

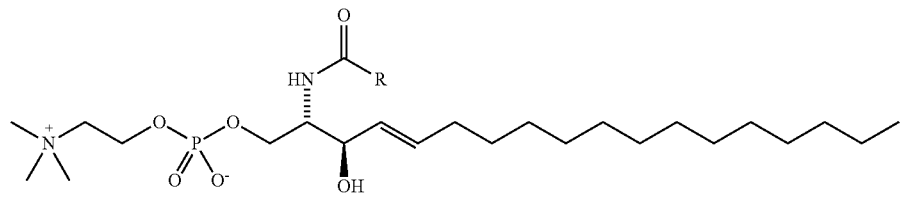

The R moiety is a fatty acid, typically a naturally occurring fatty acid or a derivative of a naturally occurring fatty acid. In another embodiment, the sphingomyelin is a naturally-occurring sphingomyelin. In another embodiment, the sphingomyelin is a synthetic sphingomyelin. In another embodiment, the sphingomyelin is a deuterated sphingomyelin. In another embodiment, the sphingomyelin is labeled with any other isotope or label. In another embodiment, the sphingomyelin contains a naturally-occurring distribution of isotopes.

In another embodiment, the fatty acid moiety of a sphingomyelin of methods and compositions of the present invention has at least 14 carbon atoms. In another embodiment, the fatty acid moiety has at least 16 carbon atoms. In another embodiment, the fatty acid moiety is chosen such that the gel-to-liquid-crystal transition temperature of the resulting matrix is at least 40° C.

Non-limiting examples of sphingomyelins are sphingomyelins modified with any of the fatty acid moieties enumerated hereinabove. In another embodiment, the sphingomyelin is any other sphingomyelin known in the art. Each sphingomyelin represents a separate embodiment of the present invention.

"Ceramide" refers to a compound having the structure:

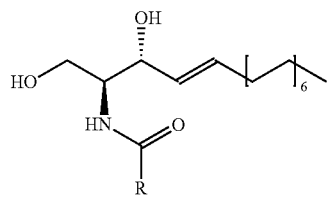

The R moiety is a fatty acid typically naturally occurring fatty acid or derivatives of naturally occurring fatty acids. In another embodiment, the fatty acid is a longer-chain (to $C_{24}$ or greater). In another embodiment, the fatty acids are saturated fatty acids. In another embodiment, the fatty acids are monoenoic fatty acids. In another embodiment, the fatty acids are n-9 monoenoic fatty acids. In another embodiment, the fatty acids contain a hydroxyl group in position 2. In another embodiment, the fatty acids are other suitable fatty acids known in the art. In another embodiment, the ceramide is a naturally-occurring ceramide. In another embodiment, the ceramide is a synthetic ceramide. In another embodiment, the ceramide is incorporated into the matrix composition. Each possibility represents a separate embodiment of the present invention.

Each sphingolipid represents a separate embodiment of the present invention.

In another embodiment, a composition of the present invention further comprises a pegylated lipid. In another embodiment, the PEG moiety has a MW of 500-5000 daltons. In another embodiment, the PEG moiety has any other suitable MW. Non-limiting examples of suitable PEG-modified lipids include PEG moieties with a methoxy end group, e.g. PEG-modified phosphatidylethanolamine and phosphatidic acid (structures A and B), PEG-modified diacylglycerols and dialkylglycerols (structures C and D), PEG-modified dialkylamines (structure E) and PEG-modified 1,2-diacyloxypropan-3-amines (structure F) as depicted below. In another embodiment, the PEG moiety has any other end group used in the art. In another embodiment, the pegylated lipid is selected from the group consisting of a PEG-modified phosphatidylethanolamine, a PEG-modified phosphatidic acid, a PEG-modified diacylglycerol, a PEG-modified dialkylglycerol, a PEG-modified dialkylamine, and a PEG-modified 1,2-diacyloxypropan-3-amine. In another embodiment, the pegylated lipid is any other pegylated phospholipid known in the art. Each possibility represents a separate embodiment of the present invention.

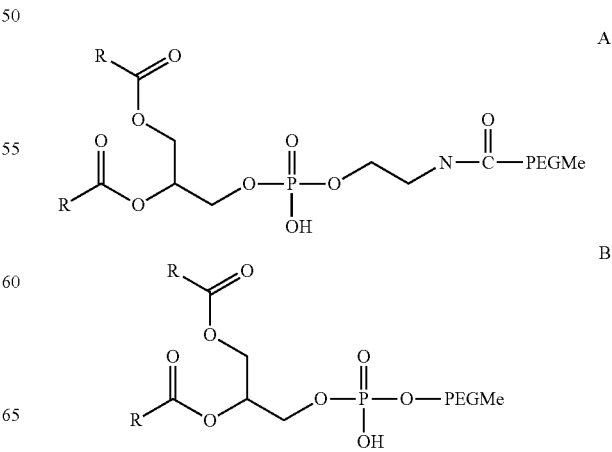

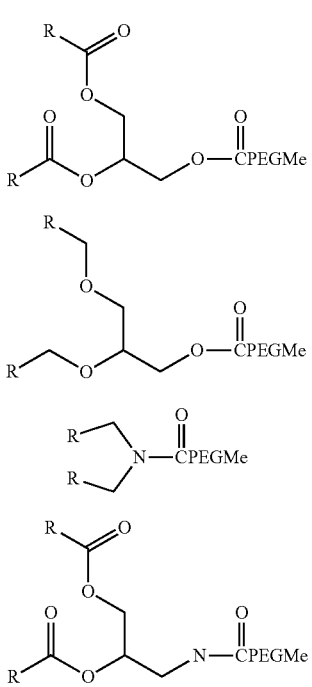

Preferably, the pegylated lipid is present in an amount of less than 10 mole percent of total lipids in the matrix composition. In another embodiment, the percentage is less than 9 mole % of the total lipids. In another embodiment, the percentage is less than 8 mole %. In another embodiment, the percentage is less than 7 mole %. In another embodiment, the percentage is less than 6 mole %. In another embodiment, the percentage is less than 5 mole %. In another embodiment, the percentage is less than 4 mole %. In another embodiment, the percentage is less than 3 mole %. In another embodiment, the percentage is less than 2 mole %. In another embodiment, the percentage is less than 1 mole %. Each possibility represents a separate embodiment of the present invention.

Polymers

According to some embodiments, the non-biodegradable polymer may be selected yet not limited to polyethylene glycol, polyethylene glycol (PEG) acrylate, polymethacrylates (e.g. PEG methacrylate, polymethylmethacrylate, polyethylmethacrylate, polybutylmethacrylate, poly-2-ethylhexylmethacrylate, polylaurylmethacrylate, polyhydroxyethyl methacrylate), poly-methylacrylate, 2-methacryloyloxyethylphosphorylcholine (MPC), polystyrene, derivatized polystyrene, polylysine, poly N-ethyl-4-vinyl-pyridinium bromide, silicone, ethylene-vinyl acetate copolymers, polyethylenes, polypropylenes, polytetrafluoroethylenes, polyurethanes, polyacrylates, polyvinyl acetate, ethylene vinyl acetate, polyethylene, polyvinyl chloride, polyvinyl fluoride, copolymers of polymers of ethylene-vinyl acetates and acyl substituted cellulose acetates, poly(vinyl imidazole), chlorosulphonate polyolefins, polyethylene oxide, and mixtures thereof.

According to particulate embodiment, the non-biodegradable polymer is polyethylene glycol. Polyethylene glycol refers to an oligomer or polymer of ethylene oxide. According to particular embodiment, the non-biodegradable polymer comprises polyethylene glycol having a molecular weight from about 1000 to about 20000; alternatively, between 2000 to about 10000. According to some exemplary embodiments, the non-biodegradable polymer is PEG having a molecular weight between about 4000 and about 8000.

According to some embodiments, the matrix composition may further comprise a biodegradable polymer. According to some embodiments, the matrix composition may comprise a biodegradable polymer other than a polyester. According to some other embodiments, the biodegradable polymer is selected from the group consisting of poly(caprolactone), polycarbonates, polyesteramides, polyanhydrides, poly(amino acid)s, polycyanoacrylates, polyamides, polyacetals, poly(ether ester)s, poly(dioxanone)s, poly(alkylene alkylate)s, biodegradable polyurethanes, blends and copolymers thereof. According to some other embodiments, the biodegradable polymer is a polyester. Non limiting examples of polyesters include PLA (polylactic acid), PGA (polyglycolic acid) and PLGA (poly(lactic-co-glycolic acid). According to some embodiment, the PLGA has a 1:1 lactic acid/glycolic acid ratio. In another embodiment, the ratio is 60:40. In another embodiment, the ratio is 70:30. In another embodiment, the ratio is 80:20. In another embodiment, the ratio is 90:10. In another embodiment, the ratio is 95:5. In another embodiment, the ratio is another ratio appropriate for an extended in vivo release profile, as defined herein. In another embodiment, the ratio is 50:50. The PLGA may be either a random or block copolymer. Each possibility represents a separate embodiment of the present invention. In another embodiment, the biodegradable polyester may be selected from the group consisting of a polycaprolactone, a polyhydroxyalkanoate, a polypropylenefumarate, a polyorthoester, a polyanhydride, and a polyalkylcyanoacrylate, provided that the polyester contains a hydrogen bond acceptor moiety. In another embodiment, the biodegradable polyester is a block copolymer containing a combination of any two monomers selected from the group consisting of a PLA, PGA, a PLGA, polycaprolactone, a polyhydroxyalkanoate, a polypropylenefumarate, a polyorthoester, a polyanhydride, and a polyalkylcyanoacrylate. In another embodiment, the biodegradable polyester is a random copolymer containing a combination of any two of the monomers listed above. Each possibility represents a separate embodiment of the present invention.

The molecular weight (MW) of a non-biodegradable polymer of methods and compositions of the present invention is, in another embodiment, between about 1-40 KDa. In another embodiment, the MW is between about 4-50 KDa. In another embodiment, the MW is between about 15-40 KDa. In another embodiment, the MW is between about 20-40 KDa. In another embodiment, the MW is between about 15-35 KDa. In another embodiment, the MW is between about 10-35 KDa. In another embodiment, the MW is between about 10-30 KDa. In another embodiment, the MW is between about 1-10 KDa. In another embodiment, the MW is between about 1-5 KDa. In another embodiment, the MW is between about 2-5 KDa. In another embodiment, a mixture of non-biodegradable polymers of different MW is utilized. In another embodiment, a mixture of non-biodegradable polymer and a biodegradable polyer of different MW may be utilized. In another embodiment, the different polymers both have a MW in one of the above ranges. Each possibility represents a separate embodiment of the present invention.

Antibiotics

The antibiotic of methods and compositions of the present invention is, in another embodiment, doxycycline. In another embodiment, the antibiotic is a hydrophobic tetracycline. Non-limiting examples of hydrophobic tetracycline are 6-demethyl-6-deoxytetracycline, 6-methylene tetracycline, minocycline (also known as 7-dimethylamino-6-demethyl-6-deoxytetracycline), and 13-phenylmercapto-a-6-deoxytetracycline. In another embodiment, the antibiotic is selected from the group consisting of doxycycline, tetracycline, and minocycline. In another embodiment, the antibiotic is integrated into the matrix composition.

In another embodiment, the antibiotic is selected from the group consisting of amoxicillin, amoxicillin/clavulanic acid, penicillin, metronidazole, clindamycine, chlortetracycline, demeclocycline, oxytetracycline, amikacin, gentamicine, kanamycin, neomycin, netilmicin, streptomycin, tobramycin, cefadroxil, cefazolin, cephalexin, cephalothin, cephapirin, cephradine, cefaclor, cefamandole, cefametazole, cefonicid, cefotetan, cefoxitine, cefpodoxime, cefprozil, cefuroxime, cefdinir, cefixime, cefoperazone, cefotaxime, ceftazidime, ceftibuten, ceftizoxime, ceftriaxone, cefepime, azithromycin, clarithromycin, dirithromycin, erythromycin, lincomycin, troleandomycin, bacampicillin, carbenicillin, cloxacillin, dicloxacillin, meticillin, mezlocillin, nafcillin, oxacillin, piperacillin, ticarcillin, cinoxacin, ciprofloxacin, enoxacin, grepafloxacin, levofloxacin, lomefloxacin, nalidixic acid, norfloxacin, ofloxacin, sparfloxacin, sulfisoxazole, sulfacytine, sulfadiazine, sulfamethoxazole, sulfisoxazole, dapson, aztreonam, bacitracin, capreomycin, chloramphenicol, clofazimine, colistimethate, colistin, cycloserine, fosfomycin, furazolidone, methenamine, nitrofurantoin, pentamidine, rifabutin, rifampin, spectinomycin, trimethoprim, trimetrexate glucuronate, and vancomycin.

In another embodiment, the biologically active ingredient is an antiseptic drug such as chlorhexidine.

Each antibiotic represents a separate embodiment of the present invention.

NSAID's

Any suitable NSAID may be integrated into the matrix composition for sustained and/or controlled release. The NSAID of methods and compositions of the present invention is, in one embodiment, flurbiprofen. In another embodiment, the NSAID is selected from the group consisting of ibuprofen and flurbiprofen. In another embodiment, the NSAID is selected from the group consisting of ibuprofen, flurbiprofen, aminosalicylate sodium, choline magnesium trisalicylate, choline salicylate, diclofenac, diflunisal, etodolac, fenoprofen, indomethacin, ketoprofen, ketolac tromethamine, magnesium salicylate, meclofenamate, mefenamic acid, nabumetone, naproxen, oxaprozin, oxyphenbutazone, piroxicam, salsalate, sulindac, tolmetin.

Each NSAID represents a separate embodiment of the present invention.

Steroids

In another embodiment, the active agent of methods and compositions of the present invention is a steroid. According to one embodiment the steroid is a steroidal anti-inflammatory drug. Non limiting examples of steroidal anti-inflammatory drugs (SAIDs) to be used in the formulations of the present invention include, but are not limited to, Corticosteroids such as: betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide, cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol.

Anti-Cancer Agents

As referred to herein, the term "anti-cancer agent" refers to any type of agent that may be used in the treatment of cancer and/or cancer related conditions. The anti-cancer reagent may include any naturally occurring or synthetically produced molecule that is capable of affecting directly or indirectly the growth and/or viability of cancer cells, cancer tumor, and/or cancer related conditions and symptoms. The anti-cancer agent may include, for example, a naturally occurring protein or peptide, a modified protein or peptide, a recombinant protein, a chemically synthesized protein or peptide, a low oral bioavailability protein or peptide, a chemical molecule, a synthetic chemical molecule, a chemotherapeutic drug, a biologically therapeutic drug, and the like, or any combination thereof. The anti-cancer reagent may be cytotoxic (toxic to cells) and/or cytostatic (suppress cell growth) and/or antiproliferative to the cancer cells and may exert its effect on cancer cells directly and/or indirectly. According to some embodiments, the anti-cancer reagent may be administered alone and/or in combination and/or before and/or after one or more additional cancer treatments. The additional cancer treatment may include such treatments as, but not limited to: chemotherapy (use of drugs to affect the cancer cells), radiotherapy (use of high-energy radiation of various sources to affect the cancer cells); biological therapy (a therapy which helps the immune system fight cancer); surgical procedures (surgical removal of the cancerous tumor); gene therapy; bone marrow transplantation; any other therapy known in the art, or any combination thereof.

Non limiting examples of anti-cancer reagents and chemotherapeutic drugs may include such drugs as, but not limited to: Alkaloids, such as, but not limited to: Docetaxel, Etoposide, Irinotecan, Paclitaxel, Teniposide, Topotecan, Vinblastine, Vincristine, Vindesine; Alkylating agents, such as, but not limited to: Busulfan, Improsulfan, Piposulfan, Benzodepa, Carboquone, Meturedepa, Uredepa, Altretamine, triethylenemelamine, Triethylenephosphoramide, Triethylenethiophosphoramide, Chlorambucil, Chloranaphazine, Cyclophosphamide, Estramustine, Ifosfamide, Mechlorethamine, Mechlorethamine Oxide Hcl, Melphalan, Novemebichin, Perfosfamide Phenesterine, Prednimustine, Trofosfamide, Uracil Mustard, Carmustine, Chlorozotocin, Fotemustine, Lomustine, Nimustine, Semustine Ranimustine, Dacarbazine, Mannomustine, Mitobronitol, Mitolactol, Pipobroman, Temozolomide; Antibiotics and analogs, such as, but not limited to: Aclacinomycins, Actinomycins, Anthramycin, Azaserine, Bleomycins, Cactinomycin, Carubicin, Carzinophilin, Cromomycins, Dactinomycins, Daunorubicin, 6-Diazo-5-oxo-L-norleucine, Doxorubicin, Epirubicin, Idarubicin, Menogaril, Mitomycins, Mycophenolic Acid, Nogalamycine, Olivomycins, Peplomycin, Pirarubicin, Plicamycin, Porfiromycin, Puromycine, Streptonigrin, Streptozocin, Tubercidin, Zinostatin, Zorubicin; Antimetabolites, such as, but not limited to: Denopterin, Edatrexate, Methotrexate, Piritrexim, Pteropterin, Tomudex, Trimetrexate, Cladridine, Fludarabine, 6-Mercaptopurine, Pentostatine Thiamiprine, Thioguanine, Ancitabine, Azacitidine, 6-Azauridine, Carmofur, Cytarabine, Doxifluridine, Emitefur, Floxuridine, Fluorouracil, Gemcitabine, Tegafur; Platinum complexes, such as, but not limited to: Caroplatin, Cisplatin, Miboplatin, Oxaliplatin; alkylators including, but not limited to, busulfan (Myleran, Busulfex), chlorambucil (Leukeran), ifosfamide (with or without MESNA), cyclophosphamide (Cytoxan, Neosar), glufosfamide, melphalan, L-PAM (Alkeran), dacarbazine (DTIC-Dome), and temozolamide (Temodar); anthracyclines, including, but not limited to doxorubicin (Adriamycin, Doxil, Rubex), mitoxantrone (Novantrone), idarubicin (Idamycin), valrubicin (Valstar), and epirubicin (Ellence); antibiotics, including, but not limited to, dactinomycin, actinomycin D (Cosmegen), bleomycin (Blenoxane), daunorubicin, and daunomycin (Cerubidine, DanuoXome); aromatase inhibitors, including, but not limited to anastrozole (Arimidex) and letroazole (Femara); bisphosphonates, including, but not limited to zoledronate (Zometa); cyclooxygenase inhibitors, including, but not limited to, celecoxib (Celebrex); estrogen receptor modulators including, but not limited to tamoxifen (Nolvadex) and fulvestrant (Faslodex); folate antagonists including, but not limited to methotrexate and tremetrexate; inorganic aresenates including, but not limited to arsenic trioxide (Trisenox); microtubule inhibitors (e.g. taxanes) including, but not limited to vincristine (Oncovin), vinblastine (Velban), paclitaxel (Taxol, Paxene), vinorelbine (Navelbine), epothilone B or D or a derivative of either, and discodermolide or its derivatives, nitrosoureas including, but not limited to procarbazine (Matulane), lomustine, CCNU (CeeBU), carmustine (BCNU, BiCNU, Gliadel Wafer), and estramustine (Emcyt); nucleoside analogs including, but not limited to mercaptopurine, 6-MP (Purinethol), fluorouracil, 5-FU (Adrucil), thioguanine, 6-TG (Thioguanine), hydroxyurea (Hydrea), cytarabine (Cytosar-U, DepoCyt), floxuridine (FUDR), fludarabine (Fludara), pentostatin (Nipent), cladribine (Leustatin, 2-CdA), gemcitabine (Gemzar), and capecitabine (Xeloda); osteoclast inhibitors including, but not limited to pamidronate (Aredia); platinum containing compounds including, but not limited to cisplatin (Platinol) and carboplatin (Paraplatin); retinoids including, but not limited to tretinoin, ATRA (Vesanoid), alitretinoin (Panretin), and bexarotene (Targretin); topoisomerase 1 inhibitors including, but not limited to topotecan (Hycamtin) and irinotecan (Camptostar); topoisomerase 2 inhibitors including, but not limited to etoposide, VP-16 (Vepesid), teniposide, VM-26 (Vumon), and etoposide phosphate (Etopophos); tyrosine kinase inhibitors including, but not limited to imatinib (Gleevec); various other proteins including monoclonal antibodies, peptides and enzymes, various other molecules, such as, for example, Super Oxide dismutase (SOD), leptin; flavanoids; or any combinations thereof.

Non limiting examples of anti-cancer agents and biological therapies that may be used according to some embodiments, may include, such therapies and molecules as, but not limited to: administration of an immunomodulatory molecule, such as, for example, a molecule selected from the group consisting of tumor antigens, antibodies, cytokines (such as, for example, interleukins (such as, for example, interleukin 2, interleukin 4, interleukin 12), interferons (such as, for example, interferon El interferon D, interferon alpha), tumor necrosis factor (TNF), granulocyte macrophage colony stimulating factor (GM-CSF), macrophage colony stimulating factor (M-CSF), and granulocyte colony stimulating factor (G-CSF)), tumor suppressor genes, chemokines, complement components, complement component receptors, immune system accessory molecules, adhesion molecules, adhesion molecule receptors, agents affecting cell bioenergetics, or any combinations thereof.

Osteogenic Factors

In another embodiment, the active agent of methods and compositions of the present invention is a compound which induces or stimulates the formation of bone. In another embodiment the active agent is osteogenic factor. In another embodiment, the osteogenic factor refers to any peptide, polypeptide, protein or any other compound or composition which induces or stimulates the formation of bone. In another embodiment, the osteogenic factor induces differentiation of bone repair cells into bone cells, such as osteoblasts or osteocytes. In another embodiment the osteogenic factor is selected from the group consisting of TGF-beta, BMP and FGF. In another embodiment the osteogenic factor is encapsulated within the matrix composition of the present invention in a concentration sufficient to induce differentiation of bone repair cells into bone cells which form bone.

Bone Resorption Inhibitors

In another embodiment, the active agent of methods and compositions of the present invention is a compound useful for supporting bone recovery. In another embodiment, the active agent is a bone resorption inhibitor. In another embodiment, the active agent is a bone density conservation agent. In another embodiment, the compound is selected from the group consisting of osteoprotegerin (OPG), BMP-2, BMP-4, vascular endothelial growth factor (VEGF), alendronate, etidronate disodium, pamidronate, risedronate, and tiludronate. In another embodiment, the compound is osteoprotegerin (OPG), a naturally secreted decoy receptor that inhibits osteoclast maturation and activity and induces osteoclast apoptosis. In another embodiment, the active agent is a bone restructuring element. Non-limiting examples of bone restructuring elements are BMP peptides. Each possibility represents a separate embodiment of the present invention.

In another embodiment, the compound is a bone morphogenetic protein (BMP). In another embodiment, the compound is selected from the group consisting of BMP-2 and BMP-4, which accelerate osteoblast activity.

In another embodiment, the compound is vascular endothelial growth factor (VEGF).

In another embodiment, the compound is an estrogen. In another embodiment, the compound is selected from the group consisting of bisphosphonate derivative. In another embodiment, the bisphosphonate derivative is selected from the group consisting of alendronate, etidronate disodium, pamidronate, risedronate, and tiludronate.

Each compound represents a separate embodiment of the present invention.

Anti-Fungal Agents

In another embodiment, the biologically active ingredient is an antifungal drug, e.g. amphotericin B cholesteryl sulfate complex, natamycin, amphotericin, clotrimazole, nystatin, amphotericin B lipid complex, fluconazole, flucytosine, griseofulvin, itraconazole, ketoconazole, benzoic acid and salicylic acid, betamethasone and clotrimazole, butenafine, carbol-fuchsin, ciclopirox, clioquinol, clioquinol and hydrocortisone, clotrimazole, econazole, gentian violet, haloprogin, iodoquinol and hydrocortisone, ketoconazole, miconazole, naftifine, nystatin, nystatin and triamcinolone, oxiconazole, sodium thiosulfate, sulconazole, terbinafine, tolnaftate, triacetin, undecylenic acid and derivatives thereof, butoconazole, clotrimazole, sulfanilamide, terconazole, and tioconazole.

Targeting Moieties

In another embodiment, a matrix composition of methods and compositions of the present invention further comprises a targeting moiety capable of interacting with a target molecule. Preferably the target molecule is selected from the group consisting of a collagen molecule, a fibrin molecule and a heparin. In another embodiment, the target molecule is another surface molecule that forms part of the extracellular matrix (ECM) of a target cell. ECM is produced and assembled locally by cells. The most important cells involved in assembling and maintaining ECM are fibroblasts. ECM contains polysaccharide chains called GAGs (glyosaminoglycans) and various protein fibers e.g., collagen, elastin, fibronectin and laminin.

In another embodiment, the targeting moiety is a fibronectin peptide. Fibronectin is a high-molecular-weight glycoprotein that binds ECM components such as collagen, fibrin and heparin. In another embodiment, the targeting moiety is another targeting moiety capable of interaction with a target molecule selected from the group consisting of a collagen molecule, a fibrin molecule and a heparin. Each possibility represents a separate embodiment of the present invention.

"Fibronectin peptide" refers, in another embodiment, to a full-length fibronectin protein. In another embodiment, the term refers to a fragment of fibronectin. In another embodiment, the fragment includes the collagen binding domain. Collagen binding domains of fibronectin molecules are well known in the art, and are described, for example, in Hynes, R O (1990). Fibronectins. New York: Springer-Verlag and in Yamada, K M and Clark, R A F (1996). Provisional matrix. In The Molecular and Cellular Biology of Wound Repair (ed. R. A. F. Clark), pp. 51-93. New York: Plenum Press. Each possibility represents a separate embodiment of the present invention.

In another embodiment, the targeting moiety is incorporated into the matrix composition. In another embodiment, the targeting moiety is modified to confer ability to incorporate into the lipid matrix. In another embodiment, the modification comprises binding to a lipid moiety. A non-limiting example of a lipid moiety is hydrogenated phosphatidylethanolamine (HPE). However, any lipid moiety capable of incorporation into the lipid matrix is suitable. In another embodiment, the targeting moiety is able to be incorporated into the lipid matrix without modification. In another embodiment, the targeting moiety is attached to the surface of a matrix composition of the present invention. In another embodiment, the targeting moiety is bound to the surface of the matrix composition or vesicle by a hydrophobic anchor covalently bound to the targeting moiety. In another embodiment, the targeting moiety is bound to the lipid vesicles by a hydrophobic anchor. In another embodiment, the targeting moiety is included during the preparation of the matrix composition, allowing it to be located in deeper layers, as well as on the surface of the matrix. Each possibility represents a separate embodiment of the present invention.

In one embodiment, the target molecule is a collagen. Collagens are well known in the art, and are described, for example, in Khoshnoodi J et al (Molecular recognition in the assembly of collagens: terminal noncollagenous domains are key recognition modules in the formation of triple helical protomers. J Biol. Chem. 281(50):38117-21, 2006). Each possibility represents a separate embodiment of the present invention.

In one embodiment, the target molecule is a fibrin. Fibrins are well known in the art, and are described, for example, in Valenick L V et al (Fibronectin fragmentation promotes alpha4beta1 integrin-mediated contraction of a fibrin-fibronectin provisional matrix. Exp Cell Res 309(1):48-55, 2005) and Mosesson M W (Fibrinogen and fibrin structure and functions. J Thromb Haemost 3(8):1894-904, 2005). Each possibility represents a separate embodiment of the present invention.

In one embodiment, the target molecule is a heparin. Heparins are well known in the art, and are described, for example, in Mosesson M W (Fibrinogen and fibrin structure and functions. J Thromb Haemost 3(8):1894-904, 2005). Each possibility represents a separate embodiment of the present invention.

Additional Components

In another embodiment, a matrix composition of methods and compositions of the present invention further comprises a free fatty acid. In another embodiment, the free fatty acid is an omega-6 fatty acid. In another embodiment, the free fatty acid is an omega-9 fatty acid. In another embodiment, the free fatty acid is selected from the group consisting of omega-6 and omega-9 fatty acids. In another embodiment, the free fatty acid has 14 or more carbon atoms. In another embodiment, the free fatty acid has 16 or more carbon atoms. In another embodiment, the free fatty acid has 16 carbon atoms. In another embodiment, the free fatty acid has 18 carbon atoms. In another embodiment, the free fatty acid has 16-22 carbon atoms. In another embodiment, the free fatty acid has 16-20 carbon atoms. In another embodiment, the free fatty acid has 16-18 carbon atoms. In another embodiment, the free fatty acid has 18-22 carbon atoms. In another embodiment, the free fatty acid has 18-20 carbon atoms. In another embodiment, the free fatty acid is linoleic acid. In another embodiment, the free fatty acid is linolenic acid. In another embodiment, the free fatty acid is oleic acid. In another embodiment, the free fatty acid is selected from the group consisting of linoleic acid, linolenic acid, and oleic acid. In another embodiment, the free fatty acid is another appropriate free fatty acid known in the art. In another embodiment, the free fatty acid adds flexibility to the matrix composition. In another embodiment, the free fatty acid slows the in vivo release rate. In another embodiment, the free fatty acid improves the consistency of the in vivo controlled release. In some embodiments the fatty acid is unsaturated. In another embodiment, the free fatty acid is saturated. In another embodiment, incorporation of a saturated fatty acid having at least 14 carbon atoms increases the gel-fluid transition temperature of the resulting matrix composition.

In another embodiment, a free fatty acid is incorporated into the matrix composition. Each type of fatty acid represents a separate embodiment of the present invention.

In another embodiment, a matrix composition of methods and compositions of the present invention further comprises a tocopherol. The tocopherol of methods and compositions of the present invention is, in another embodiment, E307 (α-tocopherol). In another embodiment, the tocopherol is β-tocopherol. In another embodiment, the tocopherol is E308 (γ-tocopherol). In another embodiment, the tocopherol is E309 (δ-tocopherol). In another embodiment, the tocopherol is selected from the group consisting of α-tocopherol, β-tocopherol, γ-tocopherol, and δ-tocopherol. In another embodiment, the tocopherol is incorporated into the matrix composition. Each possibility represents a separate embodiment of the present invention.

In another embodiment, a matrix composition of methods and compositions of the present invention further comprises physiologically acceptable buffer salts, which are well known in the art. Non-limiting examples of physiologically acceptable buffer salts are phosphate buffers. A typical example of a phosphate buffer is 40 parts NaCl, 1 part KCl, 7 parts $Na_2HPO_4.2H_2O$ and 1 part $KH_2PO_4$. In another embodiment, the buffer salt is any other physiologically acceptable buffer salt known in the art. Each possibility represents a separate embodiment of the present invention.

Release Rates and General Characteristics of the Matrix Compositions

The release characteristics from the matrix compositions are designed to provide sustained release of the active agent or agents from within the matrix to the desired site of action over a prolonged period of time. The sustained release profile will provide a therapeutically effective amount of the drug at least to the local vicinity of the matrix composition for a period of days or weeks or even months. While the compositions may have a minor percentage of the active agent which is released immediately to provide a therapeutic effect to the desired local site of action, the majority of the material will be released over a prolonged period of time. Typically up to 10-20% may be released immediately from the matrix compositions. According to some embodiments the release profile of the major portion of the agents achieves zero order kinetics. According to some embodiments 40-70% of the active agent is released under zero order kinetics. According to some embodiments the release profile can be measured in vitro. According to other embodiments the release profile may be measurable in vivo. According to yet other embodiments the in vivo release will be localized and will not be reflected in systemic drug levels.

The in vivo release time of 90% of the active ingredient for matrix compositions of the present invention is preferably between 1 week and 6 months. In another embodiment, the release time is between 4 days and 6 months. In another embodiment, the release time is between 1 week and 5 months. In another embodiment, the release time is between 1 week and 5 months. In another embodiment, the release time is between 1 week and 4 months. In another embodiment, the release time is between 1 week and 3 months. In another embodiment, the release time is between 1 week and 2 months. In another embodiment, the release time is between 2 weeks and 6 months. In another embodiment, the release time is between 2 weeks and 5 months. In another embodiment, the release time is between 2 weeks and 4 months. In another embodiment, the release time is between 2 weeks and 3 months. In another embodiment, the release time is between 3 weeks and 6 months. In another embodiment, the release time is between 3 weeks and 5 months. In another embodiment, the release time is between 3 weeks and 4 months. In another embodiment, the release time is between 3 weeks and 3 months. Each possibility represents a separate embodiment of the present invention.

"Biodegradable" as used herein, refers to a substance capable of being decomposed by natural biological processes at physiological pH. "Physiological pH" refers to the pH of body tissue, typically between 6-8. "Physiological pH" does not refer to the highly acidic pH of gastric juices, which is typically between 1 and 3.

"Non-biodegradable" as used herein, refers to a substance which is not degraded or eroded under normal mammalian physiological conditions. Generally, a substance is considered non-biodegradable if it is not degraded to a significant extent (i.e., loses more than 5% of its mass and/or average polymer length) by action of biological agents, and all during the average time by which this substance will normally retain in the body following its administration.

The weight ratio of total lipids to the polymer in order to achieve lipid saturation can be determined by a number of methods, as described herein. In another embodiment, the lipid:polymer weight ratio of a composition of the present invention is between 1:1 and 9:1 inclusive. In another embodiment, the ratio is between 2:1 and 9:1 inclusive. In another embodiment, the ratio is between 3:1 and 9:1 inclusive. In another embodiment, the ratio is between 4:1 and 9:1 inclusive. In another embodiment, the ratio is between 5:1 and 9:1 inclusive. In another embodiment, the ratio is between 6:1 and 9:1 inclusive. In another embodiment, the ratio is between 7:1 and 9:1 inclusive. In another embodiment, the ratio is between 8:1 and 9:1 inclusive. In another embodiment, the ratio is between 1.5:1 and 9:1 inclusive. Each possibility represents a separate embodiment of the present invention.

In another embodiment, the melting temperature ($T_m$) of the lipids in the matrix composition of the present invention is at least 37° C. In another embodiment, the $T_m$ is at least 40° C. In another embodiment, the $T_m$ is at least 42° C. In another embodiment, the $T_m$ is at least 44° C. In another embodiment, the $T_m$ is at least 46° C. In another embodiment, the $T_n$ is at least 48° C. In another embodiment, the $T_m$ is at least 50° C. Each possibility represents a separate embodiment of the present invention.

Implants and Other Pharmaceutical Compositions

In another embodiment, a matrix composition of the present invention is in the form of an implant, following evaporation of the organic solvents. The evaporation of the solvents is typically done at temperatures ranging from 20 to 80° C. According to some embodiments, the evaporation of the solvents can be done at temperatures ranging from 20 to 60° C.

In another embodiment, the implant is homogeneous. In another embodiment, the implant is manufactured by a process comprising the step of freeze-drying the material in a mold. Each possibility represents a separate embodiment of the present invention.

In another embodiment, the present invention provides an implant comprising an antibiotic-containing matrix composition of the present invention. In another embodiment, the present invention provides an implant comprising an NSAID-containing matrix composition of the present invention. In another embodiment, the present invention provides an implant comprising a bone resorption inhibitor-containing matrix composition of the present invention. In another embodiment, the present invention provides an implant comprising a matrix composition of the present invention that contains an antibiotic and an NSAID. In another embodiment, the present invention provides an implant comprising a matrix composition of the present invention that contains an antibiotic and a bone resorption inhibitor. In another embodiment, the present invention provides an implant comprising a matrix composition of the present invention that contains a bone resorption inhibitor and an NSAID. In another embodiment, the present invention provides an implant comprising a matrix composition of the present invention that contains an antibiotic, an NSAID, and a bone resorption inhibitor. Each possibility represents a separate embodiment of the present invention.

In another embodiment, the process of creating an implant from a composition of the present invention comprises the steps of (a) creating a matrix composition according to a method of the present invention in the form of a bulk material; (b) transferring the bulk material into a mold or solid receptacle of a desired shaped; (c) freezing the bulk material; and (d) lyophilizing the bulk material.

In another embodiment, the present invention provides a pharmaceutical composition comprising a matrix composition of the present invention and a pharmaceutically acceptable excipient.

In another embodiment, a matrix composition of the present invention is in the form of microspheres, following evaporation of the organic solvents. In another embodiment, the microspheres are homogeneous. In another embodiment, the microspheres are manufactured by a process comprising the step of spray-drying. Each possibility represents a separate embodiment of the present invention.

In another embodiment, the present invention provides microspheres made of a matrix composition of the present invention. In another embodiment, the present invention provides a pharmaceutical composition comprising microspheres of the present invention and a pharmaceutically acceptable excipient. In another embodiment, the pharmaceutical composition is in a parenterally injectable form. In another embodiment, the pharmaceutical composition is in an infusible form. In another embodiment, the excipient is compatible for injection. In another embodiment, the excipient is compatible for infusion. Each possibility represents a separate embodiment of the present invention.

In another embodiment, the particle size of microspheres of the present invention is approximately 500-2000 nm. In another embodiment, the particle size is about 400-2500 nm. In another embodiment, the particle size is about 600-1900 nm. In another embodiment, the particle size is about 700-1800 nm. In another embodiment, the particle size is about 500-1800 nm. In another embodiment, the particle size is about 500-1600 nm. In another embodiment, the particle size is about 600-2000 nm. In another embodiment, the particle size is about 700-2000 nm. In another embodiment, the particles are of any other size suitable for pharmaceutical administration. Each possibility represents a separate embodiment of the present invention.

Therapeutic Methods

In another embodiment, the present invention provides a method of administering an antibiotic to a subject in need thereof, the method comprising the step of administering to the subject a matrix composition of the present invention, thereby administering an antibiotic to a subject in need thereof. In another embodiment, a pharmaceutical composition comprising the matrix composition is administered. In another embodiment, an implant comprising the matrix composition is administered. In another embodiment, an injectable formulation comprising the matrix composition is injected. Each possibility represents a separate embodiment of the present invention.

In another embodiment, the present invention provides a method of administering a non-steroidal anti-inflammatory drug (NSAID) to a subject in need thereof, the method comprising the step of administering to the subject a matrix composition of the present invention, thereby administering an NSAID to a subject in need thereof. In another embodiment, a pharmaceutical composition comprising the matrix composition is administered. In another embodiment, an implant comprising the matrix composition is administered. In another embodiment, an injectable formulation comprising the matrix composition is injected. Each possibility represents a separate embodiment of the present invention.

In another embodiment, the present invention provides a pharmaceutical composition for administering an antibiotic to a subject in need thereof, comprising a matrix composition of the present invention. In another embodiment, the pharmaceutical composition is an implant. In another embodiment, the pharmaceutical composition is an injectable composition. Each possibility represents a separate embodiment of the present invention.

In another embodiment, the present invention provides a pharmaceutical composition for administering an NSAID to a subject in need thereof, comprising a matrix composition of the present invention. In another embodiment, the pharmaceutical composition is an implant. In another embodiment, the pharmaceutical composition is an injectable composition. Each possibility represents a separate embodiment of the present invention.

In another embodiment, the present invention provides a pharmaceutical composition for co-administering an antibiotic and an NSAID to a subject in need thereof, comprising a matrix composition of the present invention. In another embodiment, the pharmaceutical composition is an implant. In another embodiment, the pharmaceutical composition is an injectable composition. Each possibility represents a separate embodiment of the present invention.

In another embodiment, the present invention provides a method of treating periodontitis in a subject in need thereof, said method comprising the step of administering to said subject a matrix composition of the present invention, thereby treating periodontitis. "Periodontitis" refers to an inflammatory disease affecting the tissues that surround and support the teeth. In another embodiment, periodontitis involves progressive loss of the alveolar bone around the teeth and may eventually lead to the loosening and subsequent loss of teeth if left untreated. Periodontitis in some cases has a bacterial etiology. In another embodiment, the periodontitis is a chronic periodontitis. In another embodiment, the periodontitis is any other type of periodontitis known in the art. Each possibility represents a separate embodiment of the present invention.

In another embodiment, the present invention provides a method of stimulating bone augmentation in a subject in need thereof, said method comprising the step of administering to said subject a matrix composition of the present invention, thereby stimulating bone augmentation. In another embodiment, the subject has a disease or disorder selected from the group consisting of osteosarcoma/malignant fibrous histiocytoma of bone (PDQ), osteosarcoma, chondrosarcoma, Ewing's sarcoma, malignant fibrous histiocytoma, fibrosarcoma and malignant fibrous histiocytoma, giant cell tumor of bone, chordoma, lymphoma, multiple myeloma, osteoarthritis, Paget's disease of bone, arthritis, degenerative changes, osteoporosis, osteogenesis imperfecta, bone spurs, renal osteodystrophy, hyperparathyroidism, osteomyelitis, enchondroma, osteochondroma, osteopetrosis, and a diabetes-associated bone or joint disorder. In another embodiment, the matrix composition is in the form of an implant. Each possibility represents a separate embodiment of the present invention.

In another embodiment, the present invention provides a method of reducing an incidence of complications from orthopedic surgery in a subject in need thereof, said method comprising the step of administering to said subject a matrix composition of the present invention, thereby reducing an incidence of complications from orthopedic surgery. In another embodiment, the orthopedic surgery is selected from the group consisting of hand surgery, shoulder and elbow surgery, total joint reconstruction (arthroplasty), pediatric orthopedics, foot and ankle surgery, spine surgery, knee arthroscopy, knee meniscectomy, shoulder arthroscopy, shoulder decompression, carpal tunnel release, knee chondroplasty, removal of a support implant, knee anterior cruciate ligament reconstruction, knee replacement, repair of femoral neck fracture, repair of trochanteric fracture, debridement of skin, muscle, or bone fracture, repair of knee menisci, hip replacement, shoulder arthroscopy/distal clavicle excision, repair of rotator cuff tendon, repair fracture of radius (bone)/ulna, laminectomy, repair of ankle fracture (bimalleolar type), shoulder arthroscopy and debridement, lumbar spinal fusion, repair fracture of the distal part of radius, low back intervertebral disc surgery, incise finger tendon sheath, repair of ankle fracture (fibula), repair of femoral shaft fracture, and repair of trochanteric fracture. In another embodiment, the matrix composition is in the form of an implant. In another embodiment, the implant is administered during the orthopedic surgery. Each possibility represents a separate embodiment of the present invention.

In another embodiment, the present invention provides a method of enhancing an effectiveness of surgical regenerative procedure in a subject in need thereof, said method comprising the step of administering to said subject a matrix composition of the present invention, thereby enhancing an effectiveness of surgical regenerative procedure. In another embodiment, the surgical regenerative procedure is a periodontal procedure. In another embodiment, the surgical regenerative procedure comprises administering an implant (an implantology procedure). In another embodiment, the implantology procedure is directed to ridge or sinus augmentation. In another embodiment, the matrix composition is in the form of an implant. In another embodiment, the implant is administered during the surgical procedure. Each possibility represents a separate embodiment of the present invention.

In another embodiment, the present invention provides a method of treating an osteomyelitis in a subject in need thereof, said method comprising the step of administering to said subject a matrix composition of the present invention, thereby treating an osteomyelitis. In another embodiment, the matrix composition is in the form of an implant. In another embodiment, the implant is administered at or near the site of osteomyelitis. Each possibility represents a separate embodiment of the present invention.

In another embodiment, a matrix composition of the present invention is administered for aiding orthopedic bone and soft tissue recovery. The compounds are administered during or after a procedure selected from the group consisting of knee arthroscopy and meniscectomy, shoulder arthroscopy and decompression, carpal tunnel release, knee arthroscopy and chondroplasty, removal of support implant, knee arthroscopy and anterior cruciate ligament reconstruction, knee replacement, repair of femoral neck fracture, repair of trochanteric fracture, debridement of skin/muscle/bone/fracture, knee arthroscopy repair of both menisci, hip replacement, shoulder arthroscopy/distal clavicle excision, repair of rotator cuff tendon, repair fracture of radius (bone)/ulna, laminectomy, repair of ankle fracture (bimalleolar type), shoulder arthroscopy and debridement, lumbar spinal fusion, repair fracture of the distal part of radius, low back intervertebral disc surgery, incise finger tendon sheath, repair of ankle fracture (fibula), repair of femoral shaft fracture, and repair of trochanteric fracture.

In another embodiment, a matrix composition of the present invention is administered for homeostasis, reducing infections and avoiding tissue adhesions by the use of products such as sponges and membranes.

In another embodiment, a matrix composition of the present invention is administered for reducing of inflammatory reaction around suture materials.

In another embodiment, a matrix composition of the present invention is administered for sustained release of pharmaceuticals in the respiratory system: the lower respiratory tract such as the lungs, bronchi and alveoli and the upper respiratory tract such as the nose, nasal cavity, ethmoidal air cells, frontal sinuses, maxillary sinus, larynx and trachea. The administration of pharmaceuticals for treatment of systemic diseases or specific respiratory diseases such as obstructive conditions, restrictive conditions, vascular diseases, environmental, and infectious, for example, treatment of sinusitis.

In another embodiment, a matrix composition of the present invention is administered for sustained release of pharmaceuticals in the gastrointestinal tract for systemic treatment and specific gastro intestinal tract diseases.

Methods of Making Matrix Compositions

In order to obtain the compositions of the invention any suitable method may be employed that will yield a homogeneous dispersion of the polymer and the lipids in a water resistant matrix. Advantageously according to some embodiments the methods employed avoid the use of water at any stage of the manufacturing process.

According to some embodiments the polymer is mixed separately with appropriate selected volatile organic solvent(s) on the one hand and the phospholipids together with the active pharmaceutical agent are mixed with its appropriate selected solvent(s) or solvents prior to mixing together with the polymer.

In certain embodiments, the present invention provides a method of producing a matrix composition, the method comprising the steps of:

(a) mixing into a first volatile organic solvent: (i) a non-biodegradable polymer and (ii) sterol; and (b) mixing separately into a second volatile organic solvent: (i) an active agent; (ii) a phosphatidylcholine and optionally (iii) a phosphatidylethanolamine; and (c) mixing and homogenizing the products resulting from steps (a) and (b).

In another embodiment, phosphatidylethanolamine is included in the volatile organic solvent of step (a) instead of or in addition to a phosphatidylethanolamine added to the volatile organic solvent of step (b). In another embodiment, the biocompatible polymer is selected from the group consisting of non-biodegradable polymer, a biodegradable polymer other than polyester and any combination thereof. In some embodiments the first volatile organic solvent is a non-polar solvent. In some embodiments the second volatile organic solvent is a water miscible solvent. In cases where the active agent is a protein or peptide it is important to select solvents that will not denature or impair the activity of the protein. In particular embodiments the active agent is selected from the group consisting of an NSAID, an antibiotic, an antifungal agent, a steroid, an anticancer agent, an osteogenic factor and a bone resorption inhibitor and mixtures thereof.

In another embodiment, the mixture of step (a) containing a volatile organic solvent is homogenized prior to mixing it with the solution of step (b). In another embodiment, the volatile organic solvent or mixture of volatile organic solvents used in step (a) may be same or different than the volatile organic solvent or mixture of organic solvents used in step (b). In another embodiment, the mixture of step (b) is homogenized prior to mixing it with the mixture of step (a). In another embodiment, the polymer in the mixture of step (a) is lipid saturated. In another embodiment, the matrix composition is lipid saturated. Preferably, the polymer and the phosphatidylcholine are incorporated into the matrix composition. In another embodiment, the active agent as well is incorporated into the matrix composition. In another embodiment, the matrix composition is in the form of a lipid-saturated matrix whose shape and boundaries are determined by the polymer. Each possibility represents a separate embodiment of the present invention.

In another embodiment, the phosphatidylethanolamine of methods and compositions of the present invention has saturated fatty acid moieties. In another embodiment, the fatty acid moieties have at least 14 carbon atoms. In another embodiment, the fatty acid moieties have 14-20 carbon atoms. Each possibility represents a separate embodiment of the present invention.

In another embodiment, the phosphatidylcholine of methods and compositions of the present invention has saturated fatty acid moieties. In another embodiment, the fatty acid moieties have at least 14 carbon atoms. In another embodiment, the fatty acid moieties have at least 16 carbon atoms. In another embodiment, the fatty acid moieties have 14-18 carbon atoms. In another embodiment, the fatty acid moieties have 16-20 carbon atoms. Each possibility represents a separate embodiment of the present invention.

In another embodiment, the weight ratio of total lipids to polymer in the first volatile organic solvent is such that the polymer in this mixture is lipid-saturated. In another embodiment for purposes of illustration, in the case wherein the polymer is predominantly 8 KDa PEG, the molar ratio of total lipids to 8 KDa PEG is typically in the range of 10-50 inclusive. In another embodiment, the molar ratio of total lipids to 8 KDa PEG is between 10-100 inclusive. In another embodiment, the molar ratio is between 20-200 inclusive. In another embodiment, the molar ratio is between 20-300 inclusive. In another embodiment, the molar ratio is between 30-400 inclusive. Each possibility represents a separate embodiment of the present invention.

This is important since the elimination of non-biodegradable polymer fragment by the kidney is limited to small fragments. In the case of PEG it is limited to chains of 5000 Dalton, and preferably up to 2000 Dalton is used. Using large polymeric chins can elevate the inner strength of the matrix, were as the resistency of the specific linker can influence the degradation rate, reflecting on the release rate of the drug.

Each of the components of the above method and other methods of the present invention is defined in the same manner as the corresponding component of the matrix compositions of the present invention.

In another embodiment, step (a) of the production method further comprises adding to the volatile organic solvent a phosphatidylethanolamine. In another embodiment, the phosphatidylethanolamine is the same phosphatidylethanolamine included in step (b). In another embodiment, the phosphatidylethanolamine is a different phosphatidylethanolamine that may be any other phosphatidylethanolamine known in the art. In another embodiment, the phosphatidylethanolamine is selected from the group consisting of the phosphatidylethanolamine of step (b) and a different phosphatidylethanolamine. Each possibility represents a separate embodiment of the present invention.

In another embodiment, step (a) of the production method further comprises adding to the volatile organic solvent a tocopherol.

In another embodiment, step (b) of the production method further comprises adding to the volatile organic solvent physiologically acceptable buffer salts. Non-limiting examples of physiologically acceptable buffer salts are phosphate buffers. A typical example of a phosphate buffer is 40 parts NaCl, 1 part KCl, 7 parts $Na_2HPO_4.2H_2O$ and 1 part $KH_2PO_4$. In another embodiment, the buffer salt is any other physiologically acceptable buffer salt known in the art. Each possibility represents a separate embodiment of the present invention.

In another embodiment, step (b) of the production method further comprises adding to the volatile organic solvent a phospholipid selected from the group consisting of a phosphatidylserine, a phosphatidylglycerol, a sphingomyelin, and a phosphatidylinositol.

In another embodiment, step (b) of the production method further comprises adding to the volatile organic solvent a sphingolipid. In another embodiment, the sphingolipid is ceramide. In another embodiment, the sphingolipid is a sphingomyelin. In another embodiment, the sphingolipid is any other sphingolipid known in the art. Each possibility represents a separate embodiment of the present invention.

In another embodiment, step (b) of the production method further comprises adding to the water-miscible, volatile organic solvent an omega-6 or omega-9 free fatty acid. In another embodiment, the free fatty acid has 16 or more carbon atoms. Each possibility represents a separate embodiment of the present invention.

In another embodiment, each step of the production method is substantially free of aqueous solution. In another embodiment, each step is substantially free of the presence of water or any aqueous solution. As provided herein, producing matrix compositions of the present invention in a water-free process enables lipid saturation. In another embodiment, each step of the production method may involve the presence of water in an amount not greater than 20% of the total liquid volume (water and organic solvents). The aqueous solution or water will be eliminated through evaporation together with the organic solvents as described below.

Upon mixing, a homogenous mixture is formed, since the polymer is lipid-saturated in the mixture of step (a). In another embodiment, the homogenous mixture takes the form of a homogenous liquid. In another embodiment, upon freeze-drying or spray-drying the mixture, vesicles are formed. Each possibility represents a separate embodiment of the present invention.

In another embodiment, the production method further comprises the step of evaporating the solvent present in the product of step (c). In another embodiment, the evaporation utilizes atomization of the mixture. In another embodiment, the mixture is atomized into dry, heated air. Typically, atomization into heated air evaporates all water immediately, obviating the need for a subsequent drying step. In another embodiment, the mixture is atomized into a water-free solvent. In another embodiment, the evaporation is performed by spray drying. In another embodiment, the evaporation is performed by freeze drying. In another embodiment, the evaporation is performed using liquid nitrogen. In another embodiment, the evaporation is performed using liquid nitrogen that has been pre-mixed with ethanol. In another embodiment, the evaporation is performed using another suitable technique known in the art. Each possibility represents a separate embodiment of the present invention.

In another embodiment, a method of the present invention further comprises the step of vacuum-drying the composition. In another embodiment, the step of vacuum-drying is performed following the step of evaporating. Each possibility represents a separate embodiment of the present invention.

In another embodiment, the method of the present invention further comprises the step of evaporating the organic volatile solvent by heating the product of step (c). The heating is continuing until the solvent is eliminated and in a typical temperature between room temperature to 80° C. In another embodiment a step of vacuum-drying is performed following the step of solvent evaporation. Each possibility represents a separate embodiment of the present invention.

Lipid Saturation and Techniques for Determining Same

"Lipid saturated," as used herein, refers to saturation of the polymer of the matrix composition with phospholipids in combination with any hydrophobic drug and targeting moiety present in the matrix, and any other lipids that may be present. As described herein, matrix compositions of the present invention comprise, in some embodiments, phospholipids other than phosphatidylcholine. In other embodiments, the matrix compositions comprise lipids other than phospholipids. The matrix composition is saturated by whatever lipids are present. "Saturation" refers to a state wherein the matrix contains the maximum amount of lipids of the type utilized that can be incorporated into the matrix. Methods for determining the polymer:lipid ratio to attain lipid saturation and methods of determining the degree of lipid saturation of a matrix are described herein. Each possibility represents a separate embodiment of the present invention.

In another embodiment, the matrix composition of methods and compositions of the present invention is substantially free of water. "Substantially free of water" refers, in another embodiment, to a composition containing less than 1% water by weight. In another embodiment, the term refers to a composition containing less than 0.8% water by weight. In another embodiment, the term refers to a composition containing less than 0.6% water by weight. In another embodiment, the term refers to a composition containing less than 0.4% water by weight. In another embodiment, the term refers to a composition containing less than 0.2% water by weight. In another embodiment, the term refers to the absence of amounts of water that affect the water-resistant properties of the composition. In another embodiment, the term refers to a composition manufactured without the use of any aqueous solvents. In another embodiment, producing the composition using a process substantially free of water, as described herein, enables lipid saturation. Lipid saturation confers upon the matrix composition ability to resist bulk degradation in vivo; thus, the matrix composition exhibits the ability to mediate extended release on a scale of several weeks or months. Each possibility represents a separate embodiment of the present invention.

In another embodiment, the matrix composition is essentially free of water. "Essentially free" refers to a composition comprising less than 0.1% water by weight. In another embodiment, the term refers to a composition comprising less than 0.08% water by weight. In another embodiment, the term refers to a composition comprising less than 0.06% water by weight. In another embodiment, the term refers to a composition comprising less than 0.04% water by weight. In another embodiment, the term refers to a composition comprising less than 0.02% water by weight. In another embodiment, the term refers to a composition comprising less than 0.01% water by weight. Each possibility represents a separate embodiment of the present invention.

In another embodiment, the matrix composition is free of water. In another embodiment, the term refers to a composition not containing detectable amounts of water. Each possibility represents a separate embodiment of the present invention.

In another embodiment, the matrix composition is dry. "Dry" refers, in another embodiment, to the absence of detectable amounts of water or organic solvent.

In another embodiment, the water permeability of the matrix composition has been minimized. "Minimizing" the water permeability refers to a process of producing the matrix composition in organic solvents, as described herein, in the presence of an amount of lipid that has been determined to minimize the permeability to penetration of added water. The amount of lipid required can be determined by hydrating the vesicles with a solution containing tritium-tagged water, as described herein.

In another embodiment, "lipid saturation" refers to filling of internal gaps (free volume) within the lipid matrix as defined by the external border of the polymeric backbone. The gaps are filled with the phospholipids in combination with other type of lipids, hydrophobic drug and targeting moiety present in the matrix, to the extent that additional lipid moieties can no longer be incorporated into the matrix to an appreciable extent.

In one embodiment, the following method is used to determine the degree of lipid saturation:

Following manufacture, vesicles are hydrated and isolated by centrifugation or filtration. Lipids that not entrapped in the vesicles form free micelles or liposomes and are located in the supernatant. The overall lipid contents of the supernatant and the vesicles are quantified. In this manner, the entrapped vs. free lipid contents are determined for various formulation containing different lipid:polymer ratios at the outset. Thus, the actual, experimental, maximum lipid/polymer ratio is determined.

In another embodiment, the following method is used to determine the degree of lipid saturation:

Following manufacture, vesicles are hydrated with a solution containing tritium-tagged water, washed with tritium-free solution, and isolated by centrifugation or filtration, and the amount of water entrapped per polymer mass is quantified. This is repeated with different lipid:polymer ratios, in order to determine the amount of lipids required to saturate the free volume in the polymeric vesicles.

"Zero-order release rate" or "zero order release kinetics" means a constant, linear, continuous, sustained and controlled release rate of the pharmaceutical active agent from the polymer matrix, i.e. the plot of amounts of pharmaceutical active agent released vs. time is linear.

EXPERIMENTAL DETAILS SECTION

Example 1

Platform Technology for Production of Drug Carrier Compositions

Overview

To produce lipid-saturated polymer matrices, two mixtures are created.

1. A non-biodegradable polymer and a sterol and/or phospholipid component are mixed with a volatile organic solvent, which is mixed to yield a solution or suspension of lipid-saturated polymer matrix, as measured by its differential scanning calorimetric (DSC) profile.

2. The active agent and a phospholipid component are mixed with a second volatile organic solvent to yield a second solution or suspension.

3. The two solutions or suspensions are combined and mixed until equilibrium is reached; the organic solvents are then evaporated, yielding a drug-containing, lipid-saturated polymer matrix.

Exemplary protocol

I. Preparation of First Solution

Stock Solutions:

Stock solution 1 (SS1): PEG 8000, 300 mg/ml in ethyl acetate.

Stock solution 2 (SS2): Cholesterol (CH), 30 mg/ml in ethyl acetate.

Stock solution 3 (SS3): Doxycycline-Hyclate (Doxy-H), 50 mg/ml in Methanol:ethyl acetate (1:1 v/v).

Solution A1: 0.2 volume of SS1 was mixed with 1 volume of SS2 (PEG 50 mg/ml, CH 25 mg/ml).

Solution A2: 0.2 volume of SS1 was mixed with 1 volume of ethyl acetate (PEG 50 mg/ml).

The mixture is mixed. The entire process is performed at room temperature. A fat-polymer matrix is thus obtained.

II. Preparation of Second Solution

Solution B1: 1,2-distearoyl-sn-glycero-3-phosphocholine (DSPC; final concentration 225 mg/ml) dissolved in 0.75 ml SS3 was mixed with 0.25 ml ethyl acetate (final Doxy-H concentration 37.5 mg/ml).

Solution B2: 1,2-dimyristoyl-sn-glycero-3-phosphocholine (DMPC; final concentration 225 mg/ml) dissolved in 0.75 ml SS3 was mixed with 0.25 ml ethyl acetate (final Doxy-H concentration 37.5 mg/ml).

Solution B3: 1,2-dipalmitoyl-sn-glycero-3-phosphocholine (DPPC; final concentration 225 mg/ml) dissolved in 0.75 ml SS3 was mixed with 0.25 ml ethyl acetate (final Doxy-H concentration 37.5 mg/ml).

Solution B4: 0.75 ml SS3 with 0.25 ml ethyl acetate (final Doxy-H concentration 37.5 mg/ml).

The mixture is mixed, homogenized or sonicated. In some cases, prior to mixing, homogenization or sonication, a non-polar, volatile organic solvent, e.g. ethyl acetate, is included with the mixture, which is stirred gently for 30 minutes. Typically the entire process is conducted at room temperature, but higher temperatures of up to 80° C. are used, typically when highly saturated lipids are used.

No water is required in the mixture.

III—Mixing the Polymer with the Drug/Protein Mixture

The second suspension (or solution) is added to the first solution under stirring. Stirring is continued for up to 5 h. The entire process is performed at room temperature and up to 60° C., all according to the specific formulation, the nature of the lipids in use and the specific drug. Alternatively, first and second solution may be vigorously mixed using a vortex followed by incubation at 45° C. for 5 minutes. The resulting mixture should be homogenous.

Solution AB: 1 volume of solution B1, B2, B3 or B4 was mixed with 1.5 volumes of solution A1. Alternatively, 1 volume of solution B4 was mixed with 1.5 volume of solution A2.

IV—Evaporation of the Solvents

In some experiments, the solution from stage III is atomized into dry, heated air.

In other experiments, the solution from stage III is atomized into ethanol covered by liquid nitrogen or only liquid nitrogen without ethanol, after which the nitrogen and/or ethanol (as above) are evaporated.

In other experiments, when coating of surfaces is performed; the suspension from stage III is mixed with the particles (e.g. tricalcium phosphate) or devices to be coated followed by evaporation of the volatile organic solvents. The entire process is performed at a temperature of 40-60° C., preferably, solvents are evaporated by incubation at a temperature of about 45° C. for about an hour or until no liquid is visualized followed by overnight vacuum.

V—Vacuum Drying

Coated particles and coated devices are vacuum-dried for storage.

Example 2

Preparation of Doxycycline Hyclate—Bone Particles Filler Formulation for Treatment of Bone Infection Using PEG and DPPC I. Preparation of First Solution/Suspension The following materials are mixed into Chloroform:
i. Poly ethylene glycol (PEG) 8000
ii Cholesterol-50% w/w vs. PEG.

The mixture is mixed until a clear solution is obtained. The entire process is performed at room temperature. A lipid-polymer combination matrix is thus obtained.

II. Preparation of Second Solution/Suspension

The following materials are mixed with a volatile organic solvent (methanol and ethyl acetate):
i Active compound—an antibiotic Doxycycline hyclate (DOX)
ii A phosphatidylcholine—DPPC (16:0) present as 300% w/w vs. PEG.

The mixture is thoroughly mixed. The entire process is conducted at room temperature.

No water is required in the mixture.

III—Mixing the First and the Second Solution

The second solution is added to the first solution while stirring. (Ratio of 3:2 v:v) Stirring is continued for one minute. The entire process is performed at a room temperature.

IV—Evaporation Following Surface Coating

In order to coat bone filler particles, the particles were added to the mixture of stage III followed by evaporation of the volatile organic solvents. The entire process was performed at a temperature of 45° C.

The ratio between the volume of the mixture of stage III and the mass of the bone particles will determine the release period of the drug post hydration of the coated particles.

V—Vacuum Drying

Coated bone particles are vacuum-dried for storage.

Example 3

Validation of the Intactness of the Ingredients of the Matrix Composition

The matrix composition ingredients (PEG, cholesterol, phospholipids and Doxy-H) were extracted by adding 0.2 ml of DCM to the dry matrix composition.

10 μL from the extract were injected onto an HPLC so as to verify the Doxy-H intactness and concentration.

5 μL of the extract were loaded on TLC sheets and run using different mobiles in order to determine the cholesterol and phospholipids stability (The mobile phase for cholesterol was: Hexan/Ether/Acetic acid, 70/30/1 (v/v/v); the mobile phase for the Phospholipids was: Chloroform/MeOH/water 65/35/4 (v/v/v)).

Results:

The Doxy-H extracted from the complex gave a single peak at 10.37 min identical to the peak of Doxy-H standard. The major peak was more than 99% pure. The cholesterol and the phospholipids gave single spot when ran on the TLC sheet, indicating that no derivates were formed during the preparation of the complex with a Rf of 0.26 for cholesterol and 0.58 for phospholipids (FIGS. 1A and B).

Example 4

Release Profile of Doxy-H from the TCP-Matrix Composition

In order to determine the release profile of the drug (Doxy-H) from the matrix composition, the matrix composition 100 mg was hydrated with 1 ml of 5% FBS in DDW.

An hour after hydration the solution was collected and the concentration of Doxy-H in the solution was determined by HPLC. This procedure was repeated daily for 20 days.

During the first 6 days the concentration of Doxy-H in the sample was determined before and after spin-down (6000 rpm for 2 min) to evaluate the amount of encapsulated Doxy-H.

Results:
(i) During the first hour 21, 24 and 30% of the trapped Doxy-H was released from PEG+CH+Doxy+DSPC matrix composition, PEG+CH+Doxy+DMPC matric composition and PEG+CH+Doxy matrix composition, respectively. It is to be emphasized that the drug detected in the hydration solution contained free drug molecules as well as drug molecules attached to small particles (micrometer in size) of the matrix. In order to determine the amount of drug released from the matrix versus drug molecules which are bound to matrix particles, the hydration solution collected was centrifuged at 6,000 RPM for 2 min, and the concentration of the drug in the solution was determined. It was found that for matrix compositions comprising phospholipids only about 50% of the drug was found in solution whereas about 50% was found in the pellet formed during spin-down (indicating the drug is attached to the matrix), while in the matrix composition without phospholipids (PEG+CH+Doxy Polypid Complex) less than 30% of drug was found in solution, whereas more than 70% was found in the pellet.

(ii) During the first 6 days, the amount of free Doxy-H released from matrix compositions comprising phospholipids (either DMPC or DSPC) was found to be the same. Yet, the total amount of drug released (free drug and drug attached to micrometer particles of the matrix) was higher in the DMPC complexes. This difference is in correlation with the lower melting point of DMPC; enhancing its dissociation from the matrix.

Figure 2A:
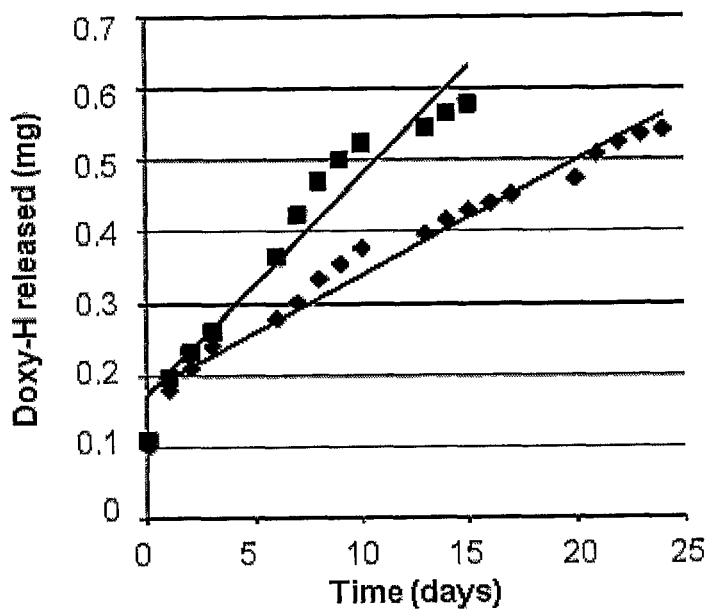
FIG. 2: The release profile of Doxy-H entrapped/encapsulated within TCP-matrix compositions after spin-down. A) Amount of Doxy-H released versus time from matrix compositions comprising PEG, CH, Doxy-H and DSPC (18:0) (large squares) and PEG, CH, Doxy-H and DMPC (14:0) (small squares); B) The percentage of Doxy-H released (of the total amount of Doxy-H encapsulated within the matrix composition comprising PEG, CH, Doxy-H and DPPC (16: 0)) versus time.
Figure 2B:
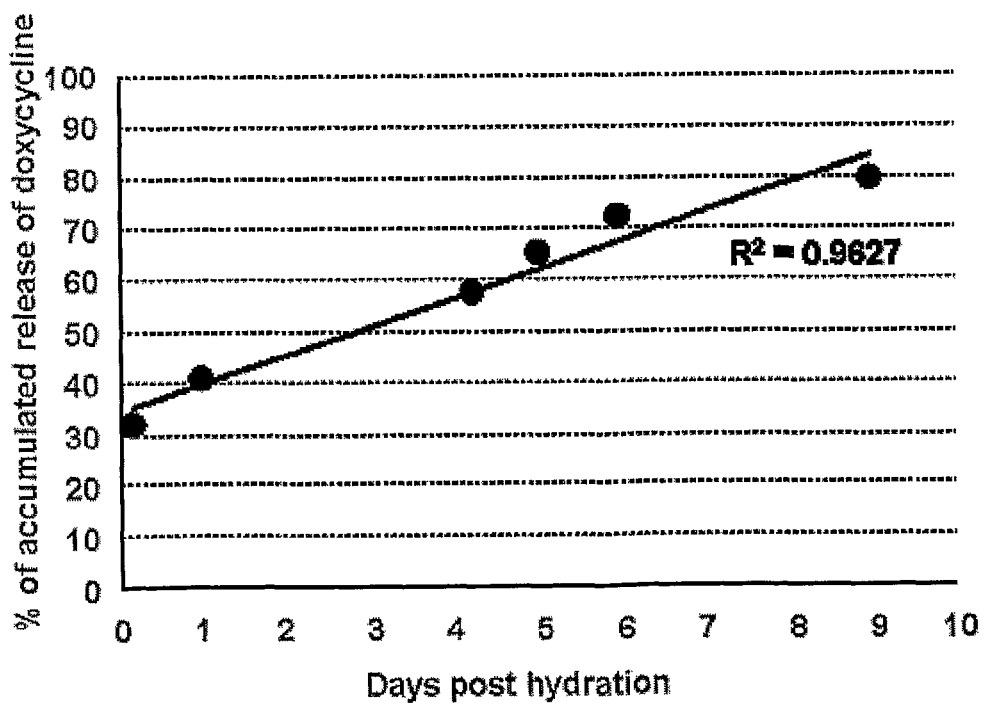

(iii) The release of Doxy-H from matrix formulations comprising phospholipids displayed a zero order kinetics starting at day 3 (FIG. 2), while the release of Doxy-H from the polymeric complex was logarithmic in nature (data not shown).

Example 5

Visualizing the Released Particles from the Matrix Composition

Figure 3A:
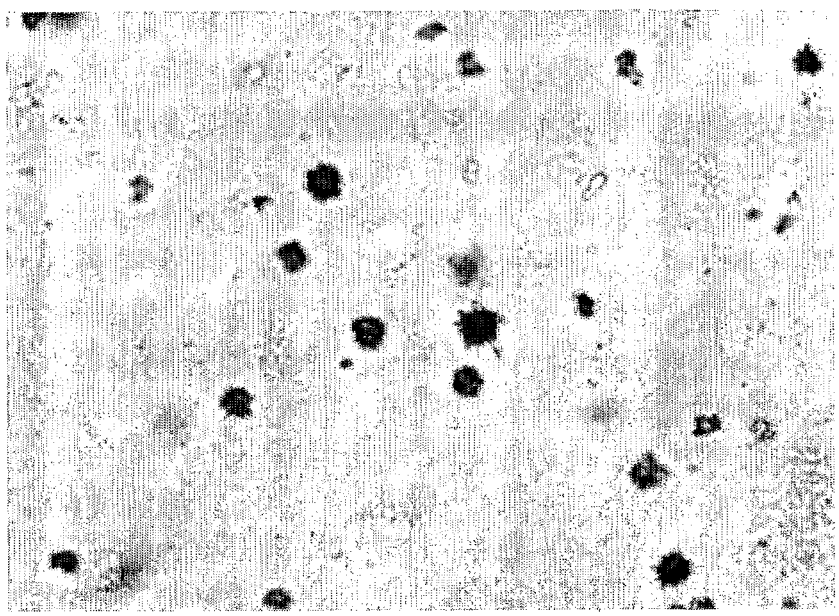
FIG. 3: Particles released after hydration of two different matrix compositions: A) matrix composition comprising PEG and Doxy-H; B) matrix composition comprising PEG, CH, Doxy-H and phospholipids.
Figure 3B:
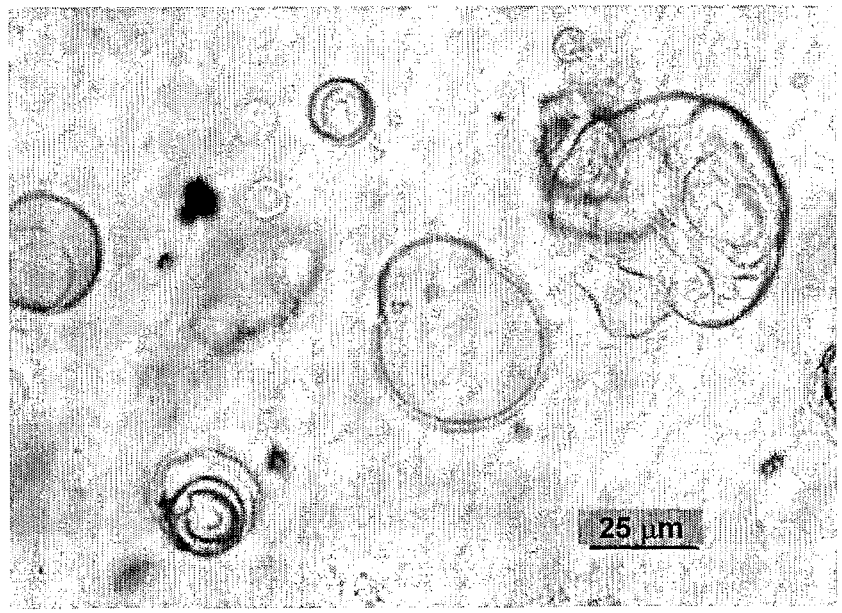

In order to determine the structure of the particles released upon hydration of the matrix composition, we have hydrated two matrix compositions (PEG+CH+DPPC+Doxy-H and PEG+Doxy-H) for 24 hours after which the supernatant was collected and looked at using a light microscope connected to a Ueye digital camera. Liposomal structures having an average size of 50 µm, mostly multi-lamelar vesicles (MLV) were detected in the supernatant of the matrix comprising PEG+CH+DPPC+Doxy-H (FIG. 3B), whereas polymeric structures having an average size of ~5 µm were detected in the supernatant of the matrix comprising PEG+Doxy-H (FIG. 3A).

Example 6

The Stability of Doxy-H in the Matrix Composition

A matrix composition PEG-CH-Doxy-H-DMPC was hydrated for 15 days. The supernatant was then removed and Doxy-H was extracted from the complex with acetonitrile: 0.01N HCl. The stability of the extracted Doxy-H was determined by HPLC.

The extracted Doxy-H was intact and no derivates were formed. The main Doxy-H peak was ~98% pure. The total amount of Doxy-H extracted was 70.44 µg. Within the first 15 days the hydrated complex released 883.579 µg. the total amount of Doxy-H released was 954 µg. This amount is ~90% of the total amount of the encapsulated Doxy-H in the formula.

Example 7

DSC Profiles of the Peg/Cholesterol/Doxy-H/DPPC Matrix Composition

The basic principle underlying the differential scanning calorimetry (DSC) technique is that, when a sample undergoes a physical transformation such as, for example, an interaction with another sample, more or less heat will need to flow to it than to the reference to maintain the temperature of the interacting samples the same as the temperature of the samples alone. Without wishing to be bound by theory or mechanism of action, this may imply, for example, that the reagent associated or assembled with the polymer alters the phase transition characteristics of the polymer, which may further imply that the reagent associated with the polymer interferes with the self assembly of the polymeric chains.

The nature of the interaction between the different components of the matrix composition according to certain embodiments of the invention was analyzed using DSC; 75 µL of either the stock solutions of the components alone as well as combinations thereof, were put into a DSC sample holder. The solvent was evaporated by incubating the holder on a dry block set to 45° C. for 30 min followed by 30 min under vacuum. DSC curves were then recorded at a scan rate of 5° C./min.

Figure 4:
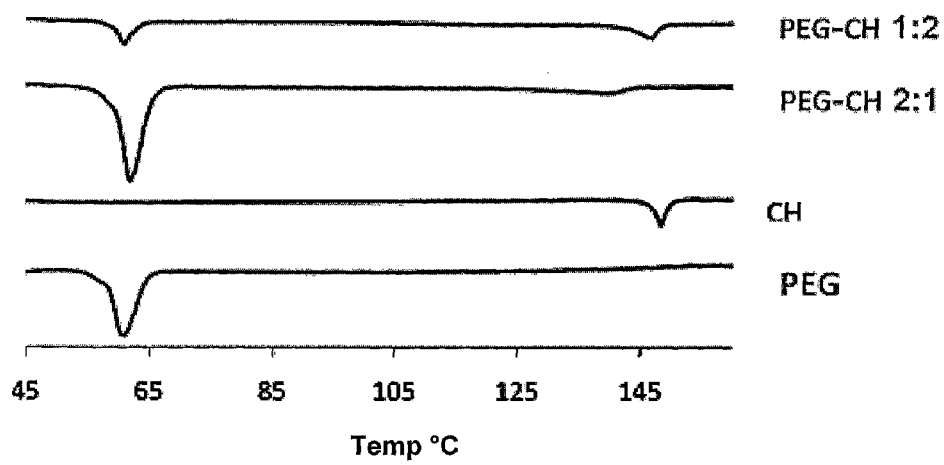
FIG. 4: Differential scanning calorimetry (DSC) scans of PEG, cholesterol and a combination of PEG and cholesterol at different ratios.
Figure 5A:
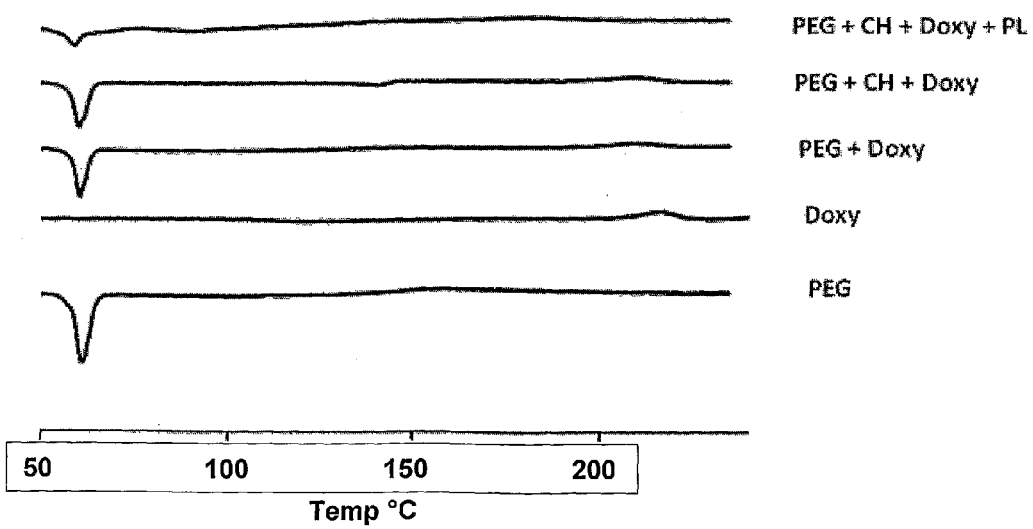
FIG. 5: Polymer: drug interaction analysis; A) DSC scans of PEG, Doxy-H, PEG-Doxy, PEG-CH-Doxy-H and PEG-CH-Doxy-H-DPPC. B) Zoom into the Doxy-H endothermic peak range (190-210° C.)
Figure 5B:
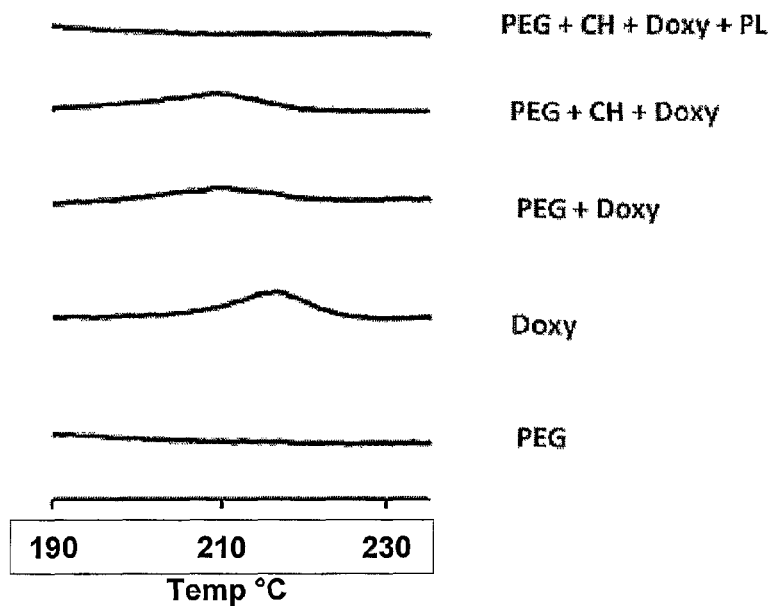
Figure 6A:
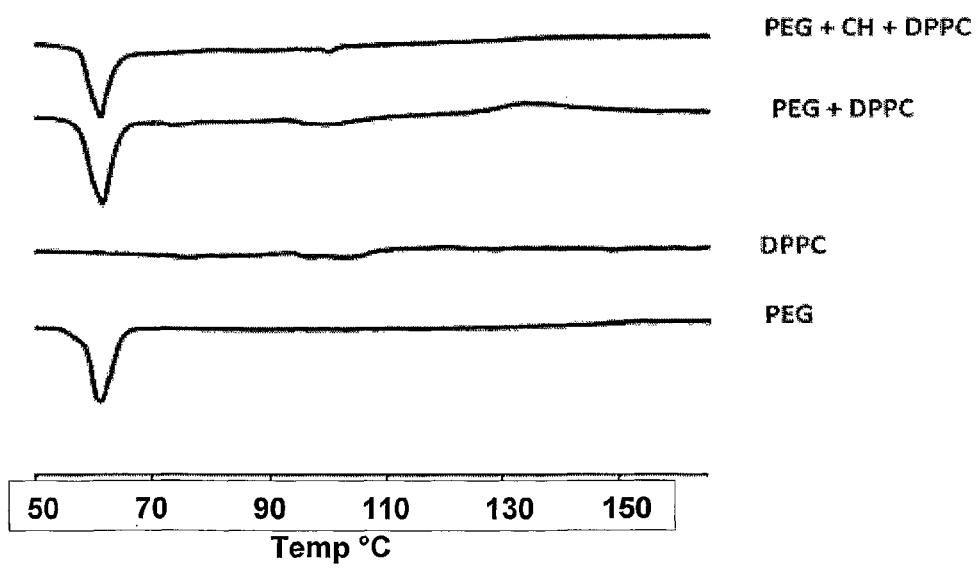
FIG. 6: Polymer: phospholipid interaction analysis; A) Full range of DSC scans of PEG, DPPC, PEG-DPPC and PEG-CH-DPPC. B) Zoom into the DPPC endothermic peak range (90-110° C.).
Figure 6B:
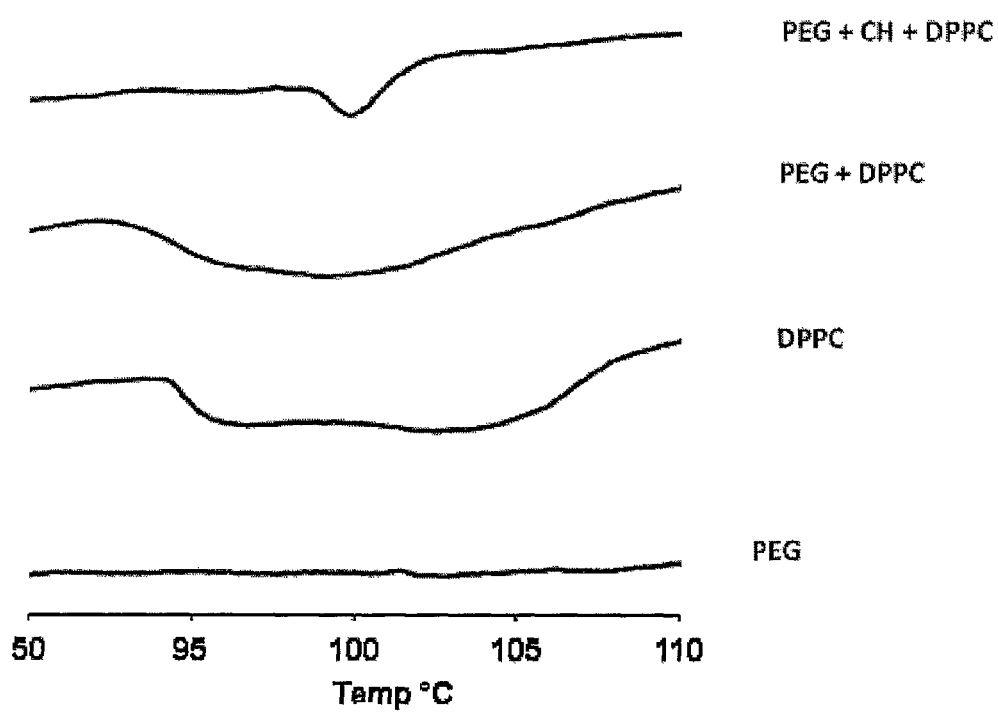

Results:
i) PEG:cholesterol interaction analysis: FIG. 4 displays DSC curves of PEG, cholesterol (CH), PEG:CH in a molar ratio of 1:10 PEG:CH (50 mg/ml and 25 mg/ml, respectively) and PEG:CH in a molar ratio of 1:40 (12.5 mg/ml and 25 mg/ml, respectively). A shift in the cholesterol melting point (from 147° C. to 124° C. is observed as well as a change in the shape of the CH peak. The melting point of CH didn't change upon increasing the ratio between PEG:CH to 1:40, yet the heat capacity of PEG has been decreased (from ~47 to 35 cal/gr).

ii) PEG: drug interaction analysis: FIG. 5A displays DSC curves of PEG, Doxy-H, PEG:Doxy-H in a molar ratio of 1:7.7 (30 and 15 mg/ml respectively), PEG:CH:Doxy-H in a molar ratio of 1:10:7.7 (30, 15 and 15 mg/ml, respectively) and PEG:CH:Doxy-H:DPPC in a molar ratio of 1:10:7.7:36 (30, 15, 15 and 90 mg/ml, respectively). A shift in the Doxy-H melting point (from 215° C. to 210° C.) is observed as well as a change in the shape of the Doxy-H peak (FIG. 5B).

iii) PEG:phospholipid interaction analysis: FIG. 6A-B displays DSC curves of PEG, DPPC, PEG:DPPC in a molar ratio of 1:32 (30 and 90 mg/ml, respectively), and PEG:CH:DPPC 1:10:32 (30, 15 and 90 mg/ml, respectively). Changes in the heat content of both PEG and DPPC are observed upon interaction (from 47 to 99.03 cal/gr for PEG, from 6.6 to 5.1 cal/gr for DPPC). The addition of CH totally eliminates the endothermic peaks of both DPPC and CH yet its addition does not affect the heat content of PEG.

Example 8

Pre-Clinical Testing of Matrix Composition of the Present Invention for Bone Recovery Animal Models:
A. Tibial osteomyelitis in rabbit
B. Bacteria: *staphylococcus aureus*

All preclinical testing is performed in accordance with the guidelines for Regulation of Animal Experiments in the State of Israel and according to the Ethics Committee of the research institution.

Test A): Determine the Relevant Bacterial Load for the Model:

1. Cause a trauma to the bone (as determined in test A)—10 animals.
2. Fill the void (injured bone) by tricalcium phosphate (TCP) material and seal it with Bone-Wax.
3. Load the site with defined amount of bacteria by injecting it into the site.
4. Duration—~22 days. Clinical signs and body weight (3× weekly) is monitored.
5. At the end of the incubation time: bleed the animal for basic Hematology & Biochemistry blood (prior to the termination of the test).
6. X-Ray of the tibia prior to the termination of the test (day ~20)
7. terminate the experiment, and harvest the tibia for bacteriological test.
8. extract the bacteria from the bone and determine the bacterial concentration (as described below)

Determination of Bacterial Concentration in the Bone Marrow:

The bone marrow and the intramedullary canal is swabbed with sterile cotton tip applicators for gross culture analysis of quality assurance. The inoculated applicator is streaked onto blood plates and then placed into 5 mL of sterile TSB. The plates and tubes are then incubated at 37° C. for 24 h and growth is recorded.

Determination of Bacterial Concentration in the Per Gram of Bone:

The bone is placed into a sterile, 50 mL centrifuge tube and weighed. The bone is then crushed and the final product weighed. Normal sterile saline, 0.9%, is added in a 3:1 ratio (3 mL saline/g of bone), and the suspensions are vortexed for 2 min. Six 10-fold dilutions of each suspension are prepared with sterile, normal saline, 0.9%. Samples (20 µl) of each dilution, including the initial suspension, are plated, in triplicate, onto blood agar plates and incubated at 37° C. for 24 h; colony forming units are counted at the greatest dilution for each tibia sample. The *S. aureus* concentration is calculated in CFU/g of bone.

Test A) Determine the Relevant Bacterial Load for the Model:

| Group | Trauma | Addition of Bacteria | No of animals | Treatment | Duration |
| --- | --- | --- | --- | --- | --- |
| A | Test | Positive | Yes (L) | 3 | TCP (control) | 22 days |
| B | Test | Positive | Yes (M) | 3 | TCP (control) | 22 days |
| C | Test | Positive | Yes (H) | 3 | TCP (control) | 22 days |
| D | Control | Negative | No | 1 | TCP (control) | 22 days |

Test B) Determine the Bactericidal Activity of the Matrix Composition of the Invention:

1. Cause a trauma to the bone (as described in test A)—13 animals
2. Fill the void (injured bone) by TCP material and seal it with Bone-Wax.
3. Loading the site with defined amount of bacteria by injecting it into the site (the load will be determine following the result of test A).
4. Duration—~22 days. Clinical signs and body weight (3× weekly) is monitored.
5. During the incubation time: bleed the animals for basic Hematology & Biochemistry blood panel at day 7 and 16 (prior to the termination of the test).
6. X-Ray of the tibia at day 1 (or 2)+at day ~20 prior to the termination of the test.
7. Terminate the experiment, and to harvest the tibia for bacteriological tests.
8. Extracting the bacteria from the bone and determining the bacterial concentration: as described above for test A.
9. Local drug concentration is assayed.

Test B) Determine the Bactericidal Activity of the Matrix Composition of the Invention (BonyPid):

| Group | Trauma | Addition of Bacteria | No of animals | Treatment | Duration |
| --- | --- | --- | --- | --- | --- |
| A | Test | Positive | Yes | 6 | BonyPid | 22 days |
| B | Test | Positive | Yes | 6 | TCP (control) | 22 days |
| C | Control | Positive | no | 1 | TCP (control) | 22 days |

Test C) Toxicology of the Matrix Composition of the Invention:

1. Cause a trauma to the bone (as described in test A)—24 animals
2. Fill the void (injured bone) by TCP material and seal it with Bone-Wax.
3. Loading the site with defined amount of bacteria by injecting it into the site (the load will be determine following the result of test A).
4. Duration—~45 days. Clinical signs and body weight (3× weekly) are monitored. Termination time is determined according to the X-Ray results taken during the incubation time.
5. During the incubation time: bleed the animals for basic Hematology & Biochemistry blood panel at day 0, 10, 30 and 45 (prior to the termination of the test).
6. The animals will be bleeding for blood-drug-concentration analysis at days 1, 3, 10, 16 and 30.
7. X-Ray of the tibia at day 2, 20, 30 and 43 prior to the termination of the test.
8. Terminate the experiment and harvest the tibia for Histology tests.
9. Histology tests for the injured site to 50% of the animals (12 animals).
10. Extracting the bacteria from the bone and determining the bacterial concentration for 50% of the animals (12 animals) as described above.

Test C) Toxicology of the Matrix Composition of the Invention (BonyPid):

| Group | Trauma | Addition of Bacteria | No of animals | Treatment | Duration |
| --- | --- | --- | --- | --- | --- |
| A | Test | Positive | Yes | 6 | BonyPid | 45 days |
| C | Test | Positive | Yes | 6 | BonyPid | 45 days |
| D | Control | Positive | no | 6 | BonyPid | 45 days |
| F | Control | Positive | no | 6 | BonyPid | 45 days |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A medical device comprising: a substrate and a biocompatible coating deposited on at least a fraction of said substrate, wherein the biocompatible coating comprises a non-liposomal matrix composition, the matrix composition comprising:
   (a) a biocompatible non-biodegradable polymer non-covalently associated with a first lipid comprising at least one sterol having a polar group;
   (b) a second lipid comprising at least one phospholipid having hydrocarbon chains of at least 14 carbons, wherein the biocompatible non-biodegradable polymer is not bonded to the second lipid; and
   (c) at least one pharmaceutically active agent;
   wherein the matrix composition is lipid saturated and when maintained in an aqueous environment provides zero-order release of least 40% the pharmaceutically active agent.

2. The medical device of claim 1, wherein said biocompatible coating includes multi-layers.

3. The medical device of claim 1, wherein said substrate is selected from orthopedic nails, orthopedic screws, orthopedic staples, orthopedic wires, orthopedic pins, metal or polymeric implants, bone filler particles, collagen and non-collagen membranes, suture materials, orthopedic cements and sponges.

4. The medical device of claim 2, wherein the substrate is bone filler particles.

5. The medical device of claim 1, wherein said phospholipid is a phosphatidylcholine having fatty acid moieties having at least 14 carbons.

6. The medical device of claim 1, wherein the matrix composition further comprises a biodegradable polymer.

7. The medical device of claim 6, wherein the non-biodegradable polymer and the biodegradable polymer form a block co-polymer.

8. The medical device of claim 1, wherein the non-biodegradable polymer is selected from the group consisting of polyethylene glycol (PEG), PEG acrylate, PEG methacrylate, methylmethacrylate, ethylmethacrylate, butylmethacrylate, 2-ethylhexylmethacrylate, laurylmethacrylate, hydroxylethyl methacrylate, 2-methacryloyloxyethylphosphorylcholine (MPC), polystyrene, derivatized polystyrene, polylysine, poly N-ethyl-4-vinyl-pyridinium bromide, polymethylacrylate, silicone, polyoxymethylene, polyurethane, polyamides, polypropylene, polyvinyl chloride, polymethacrylic acid, and derivatives thereof alone or as co-polymeric mixtures thereof.

9. The medical device of claim 1, wherein the non-biodegradable polymer is polyethylene glycol.

10. The medical device of claim 1, wherein the sterol is cholesterol, and wherein the cholesterol is present in an amount of 5-50 mole percent of the total lipid content of said matrix composition.

11. The medical device of claim 1, wherein the pharmaceutically active agent is selected from the group consisting of an antibiotic, an antifungal, a non-steroidal anti-inflammatory drug (NSAID), a steroid, an anti-cancer agent, an osteogenic factor, a bone resorption inhibitor and any combination thereof.

12. The medical device of claim 1, wherein the weight ratio of total lipids to said biocompatible polymer is between 1.5:1 and 9:1 inclusive.

13. The medical device of claim 1, wherein said matrix composition is homogeneous.

14. The medical device of claim 1, wherein the matrix composition further comprises a compound selected from the group consisting of: an additional phospholipid selected from the group consisting of a phosphatidylserine, a phosphatidylglycerol, and a phosphatidylinositol; a free fatty acid having 14 or more carbon atoms; a sphingolipid; a pegylated lipid and a tocopherol.

15. The medical device of claim 1, wherein the matrix composition further comprising a targeting moiety capable of interacting with a target molecule selected from the group consisting of a collagen molecule, a fibrin molecule and a heparin.

16. The medical device of claim 1, wherein at least 40-70% of said pharmaceutically active agent is released from the matrix composition at zero-order kinetics when said matrix is maintained in an aqueous environment.

17. A method of treating periodontitis comprising applying the medical device of claim 1 to a bone loss site of a subject in need of such treatment.

18. The method of claim 17, wherein the pharmaceutically active agent comprises an antibiotic agent, an osteogenic factor, a bone resorption inhibitor or a combination thereof.

19. A method of stimulating bone augmentation in a subject in need thereof, the method comprising the step of applying to a bone loss site in said subject the medical device of claim 1, thereby stimulating bone augmentation in the subject.

20. A method of producing the medical device of claim 1, the method comprising the steps of:
   a. mixing into a first volatile organic solvent: (i) a biocompatible non-biodegradable polymer and (ii) a first lipid comprising at least one sterol having a polar group;
   b. mixing into a second volatile organic solvent: (i) at least one pharmaceutically active agent; (ii) a second lipid selected from phospholipids having hydrocarbon chain of at least 14 carbons; and
   c. mixing the products resulting from steps (a) and (b), to produce a homogeneous mixture;
   d. adding the substrate to the homogeneous mixture of step c; and
   e. evaporating the volatile organic solvents;
   wherein each of the steps (a)-(e) is essentially free of an aqueous solution.

21. The medical device of claim 1, wherein the biocompatible non-biodegradable polymer is associated with the first lipid via hydrogen bonds.

22. The medical device of claim 1, wherein the molar ratio of the biocompatible non-biodegradable polymer to the first lipid is from 1:5 to 1:40.

23. The medical device of claim 4, further comprising non-coated bone filler particles.

24. The method of claim 17, wherein the medical device comprises bone filler particles as the substrate.

25. The method of claim 24, wherein the medical device comprises an antibiotic agent as the pharmaceutically active agent.

26. The method of claim 19, wherein the medical device comprises bone filler particles as the substrate.

27. The method of claim 26, wherein the medical device comprises an antibiotic agent as the pharmaceutically active agent.

28. The medical device of claim 1, wherein the phospholipid is selected from the group consisting of: 1,2-dimyristoyl-sn-glycero-3-phosphocholine (DMPC), 1,2-dipalmitoyl-sn-glycero-3-phosphocholine (DPPC) and 1,2-distearoyl-sn-glycero-3-phosphocholine (DSPC).

* * * * *